US008114620B2

(12) United States Patent
Pohlner et al.

(10) Patent No.: US 8,114,620 B2
(45) Date of Patent: Feb. 14, 2012

(54) DIAGNOSTIC AND THERAPEUTIC TARGET PRKX PROTEINS FOR NEURODEGENERATIVE DISEASES

(75) Inventors: Johannes Pohlner, Hamburg (DE); Heinz Von Der Kammer, Hamburg (DE)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/921,225

(22) PCT Filed: May 30, 2006

(86) PCT No.: PCT/EP2006/062741
§ 371 (c)(1),
(2), (4) Date: Feb. 26, 2008

(87) PCT Pub. No.: WO2006/128879
PCT Pub. Date: Dec. 7, 2006

(65) Prior Publication Data
US 2009/0136504 A1    May 28, 2009

(30) Foreign Application Priority Data
May 30, 2005   (EP) ..................................... 05104631

(51) Int. Cl.
*G01N 33/53*   (2006.01)
*G01N 33/567*  (2006.01)
*G01N 33/566*  (2006.01)

(52) U.S. Cl. ........ 435/7.92; 435/7.9; 435/7.8; 435/7.21; 435/7.1; 436/501; 436/503

(58) Field of Classification Search .......................... None
See application file for complete search history.

(56) References Cited

FOREIGN PATENT DOCUMENTS

| WO | 2004/020665 | 3/2004 |
| WO | 2004/112589 | 12/2004 |
| WO | 2005/119262 | 12/2005 |

OTHER PUBLICATIONS

D. Semizarov et al., "A Lineage-specific protein kinase crucial for myeloid maturation", Proc. Natl. Acad. Sci., vol. 95, pp. 15412-15417, Dec. 1998.
W. Li et al., "Profiles of PrKX expression in developmental mouse embryo and human tissues", JHC Express, pp. 1-23, Apr. 18, 2005.
K. Schiebel et al., "Abnormal XY interchange between a novel isolated protein kinase gene, PRKY, and its homologue, PRKX, accounts for one third of all (Y+)XX males and (Y−)XY females", Human Molecular Genetics, vol. 6, No. 11, pp. 1985-1989, Oct. 1997.
I. Greeve et al., "Age-Dependent Neurodegeneration and Alzheimer-Amyloid Plaque Formation in Transgenic *Drosophila*", The Journal of Neuroscience, vol. 24, No. 16, pp. 3899-3906, Apr. 21, 2004.
Database Geneseq, "Human Kinase Related Protein", XP-002362937, Apr. 22, 2004, Database Accession No. ADI36513.
B. Zimmermann et al., "PrKX is a Novel Catalytic Subunit of the cAMP-dependent Protein Kinase Regulated by the Regulatory Subunit Type I", The Journal of Biological Chemistry, vol. 274, No. 9, pp. 5370-5378, Feb. 26, 1999.
Rüdiger J. Blaschke, et al., "A Novel Murine PKA-Related Protein Kinase Involved in Neuronal Differentiation", Genomics, vol. 64, No. 2, 2000, pp. 187-194.

*Primary Examiner* — Olga N Chernyshev
(74) *Attorney, Agent, or Firm* — Wenderoth, Lind & Ponack, L.L.P.

(57) ABSTRACT

The present invention discloses a dysregulation of a PRKX gene and the protein products thereof in Alzheimer's disease patients and individuals being at risk of developing Alzheimer's disease. Based on this finding, the invention provides methods for diagnosing and prognosticating Alzheimer's disease in a subject, and for determining whether a subject is at increased risk of developing Alzheimer's disease. Furthermore, this invention provides therapeutic and prophylactic methods for treating and preventing Alzheimer's disease and related neurodegenerative disorders using a PRKX gene and its corresponding gene products. Screening methods for modulating agents of neurodegenerative diseases are also disclosed.

1 Claim, 20 Drawing Sheets

Figure 1: Identification of the differentially expressed gene PRKX by GeneChip microarray analysis

Figure 2:
Analysis of PRKX mRNA expression by quantitative PCR measured data of PRKX mRNA expression in frontal and inferior temporal cortices in Braak stages 0 – 4

| Donor | Braak stage | Frontal | Temporal |
| --- | --- | --- | --- |
| C011 | 0 | 88.8333 | 67.4087 |
| C012 | 0 | 110.8079 | 94.9113 |
| C026 | 0 | 53.9243 | 46.2760 |
| C027 | 0 | 47.5921 | 51.7613 |
| C032 | 0 | 76.9483 | 71.6816 |
| C014 | 1 | 212.5791 | 185.3968 |
| C028 | 1 | 46.8136 | 56.5168 |
| C029 | 1 | 86.6158 | 126.5573 |
| C030 | 1 | #DIV/0! | #DIV/0! |
| C036 | 1 | #DIV/0! | #DIV/0! |
| C038 | 1 | 88.8687 | 101.0214 |
| C039 | 1 | 52.7322 | 31.7496 |
| C008 | 2 | 35.5761 | 37.1341 |
| C031 | 2 | 13.7663 | 12.6466 |
| C033 | 2 | 79.7729 | 61.8957 |
| C034 | 2 | 72.2403 | 57.8616 |
| DE03 | 2 | 46.1562 | 36.7279 |
| C025 | 3 | 42.1552 | 41.9959 |
| DE07 | 3 | 110.3829 | 156.0494 |
| DE11 | 3 | 74.2368 | 84.1129 |
| C057 | 3 | 103.9013 | 100.0807 |
| P012 | 4 | 163.0308 | 210.3438 |
| P046 | 4 | 142.0928 | 169.0411 |
| P047 | 4 | 73.6209 | 102.7507 |
| P068 | 4 | 117.7727 | 115.7678 |

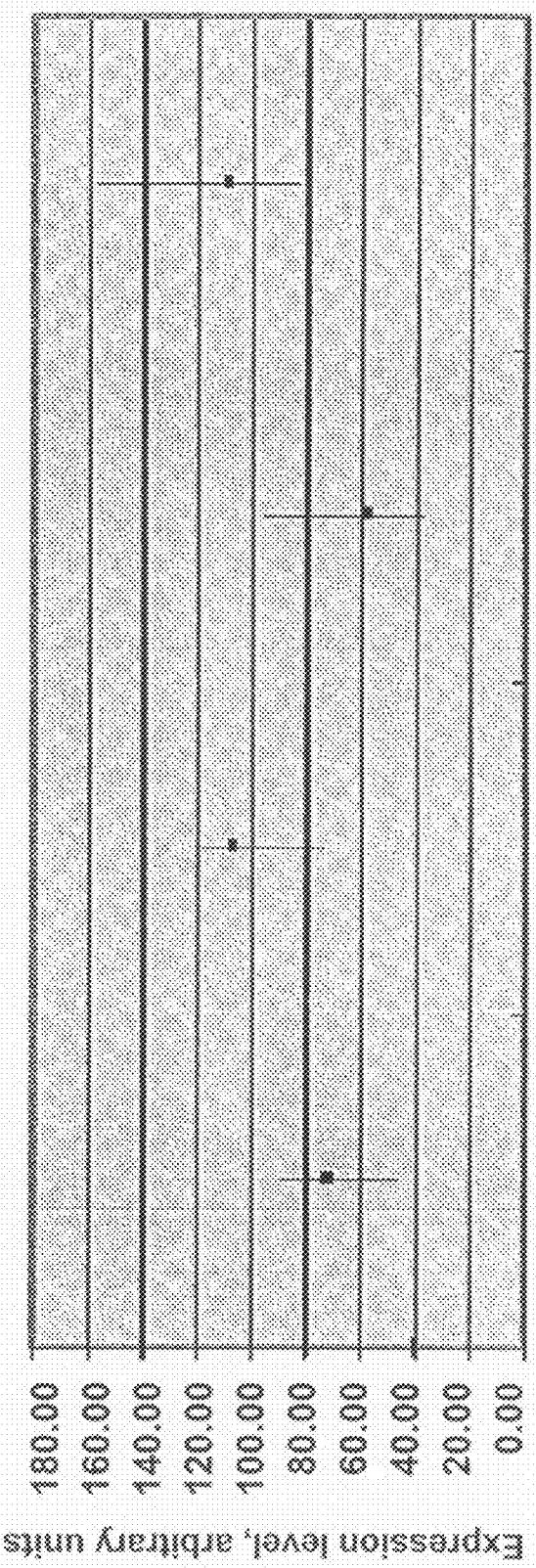
Figure 3: Statistical analysis of differential PRKX mRNA expression

Figure 4 : A) SEQ ID NO: 1, amino acid sequence of human PRKX protein

Length: 358 aa

```
  1  MEAPGLAQAA AAESDSRKVA EETPDGAPAL CPSPEALSPE PPVYSLQDFD
 51  TLATVGTGTF GRVHLVKEKT AKHFFALKVM SIPDVIRLKQ EQHVHNEKSV
101  LKEVSHPFLI RLFWTWHDER FLYMLMEYVP GGELFSYLRN RGRFSSTTGL
151  FYSAEIICAI EYLHSKEIVY RDLKPENILL DRDGHIKLTD FGFAKKLVDR
201  TWTLCGTPEY LAPEVIQSKG HGRAVDWWAL GILIFEMLSG FPPFFDDNPF
251  GIYQKILAGK IDFPRHLDFH VKDLIKKLLV VDRTRRLGNM KNGANDVKHH
301  RWFRSVDWEA VPQRKLKPPI VPKIAGDGDT SNFETYPEND WDTAAPVPQK
351  DLEIFKNF
```

Figure 4 : B) SEQ ID NO: 2, amino acid sequence of human PRKY protein

Length: 277 aa

```
  1  MEAPGPAQAA  AAESNSREVT  EDAADWAPAL  CPSPEARSPE  APAYRLQDCD
 51  ALVTMGTGTF  GRVHLVKEKT  AKHFFALKVM  SIPDVIRRKQ  EQHVHNEKSV
101  LKEVSHPFLI  RLFWTWHEER  FLYMLMEYVP  GGELFSYLRN  RGHFSSTTGL
151  FYSAEIICAI  EYLHSKEIVY  RDLKPENILL  DRDGHIKLTD  FGFAKKLVDR
201  TWTLCGTPEY  LAPEVIQSKG  HGRAVDWWAL  GILIFEMLSG  FPPFFDDNPF
251  GIYQKILAGK  LYFPRHLDFH  VKTGRMM
```

Figure 5 : A) SEQ ID NO: 3, nucleotide sequence of human PRKX cDNA

Length: 2350 bp

```
   1 GCCGCCCAGC CATTGTCCCC GTCGCTCCGT CAGCCGCGCC GGACCGCGCA
  51 CCAGGAGGCG AGAGCGCGCA TGGGGAGCCT CTGTTGATGC CGCCGCCGCG
 101 CCGCCCTCCG AGGCTGCGTC CCGGGAAGCC CGGCTCCCCG AGCGCTCCGG
 151 CCTGGCCCGG TGCCCCGGAC CTGAGTGCGT CCCCATGGAG GCGCCCGGGC
 201 TGGCCCAGGC GGCCGCGGCG GAGAGCGACT CCCGCAAGGT GGCGGAGGAG
 251 ACCCCCGACG GGGCGCCCGC GCTCTGCCCC AGCCCTGAGG CGCTGTCGCC
 301 GGAGCCGCCT GTGTACAGCC TGCAGGACTT TGACACGCTG GCCACCGTGG
 351 GCACTGGGAC GTTCGGCGG GTGCACCTGG TGAAGGAGAA GACAGCCAAG
 401 CATTTCTTCG CCCTCAAGGT GATGAGCATT CCTGACGTCA TCCGCCTAAA
 451 GCAGGAGCAA CACGTACACA ATGAGAAGTC TGTCCTGAAG GAAGTCAGCC
 501 ACCCGTTCCT CATCAGGCTG TTCTGGACGT GGCATGACGA GCGCTTCCTC
 551 TACATGCTCA TGGAGTACGT GCCGGGCGGC GAGCTCTTCA GCTACCTGCG
 601 CAACCGGGGG CGCTTCTCCA GCACCACGGG GCTCTTCTAC TCTGCAGAGA
 651 TCATCTGTGC CATCGAGTAC CTGCACTCCA AAGAGATCGT CTACAGGGAC
 701 TTGAAGCCAG AGAACATCCT GCTGGATAGG GATGGCCACA TTAAGCTCAC
 751 GGACTTTGGG TTCGCCAAGA AGCTGGTAGA CAGGACTTGG ACCCTCTGTG
 801 GAACACCCGA GTACCTAGCC CCCGAAGTCA TTCAGAGCAA GGGCCACGGA
 851 AGGGCCGTGG ACTGGTGGGC CCTCGGCATC CTGATATTCG AGATGCTTTC
 901 GGGGTTTCCT CCGTTTTTTG ATGACAACCC GTTTGGCATT TATCAGAAAA
 951 TTCTTGCAGG CAAAATAGAT TTCCCCAGAC ATTTGGATTT CCATGTAAAA
1001 GACCTCATTA AGAAACTGCT CGTGGTTGAC AGAACAAGGC GATTAGGAAA
1051 CATGAAGAAC GGGGCGAATG ATGTGAAGCA TCATCGGTGG TTCCGCTCCG
1101 TGGACTGGGA AGCTGTTCCG CAGAGAAAAC TGAAGCCTCC CATCGTGCCC
1151 AAGATAGCTG GTGACGGCGA CACTTCCAAC TTCGAAACTT ACCCTGAGAA
1201 TGACTGGGAC ACAGCCGCGC CCGTGCCGCA GAAGGATTTA GAAATCTTCA
1251 AGAATTTCTG AGGACAGGAG CTCACATCTG GAAGAAACAG GAAGATTGGA
1301 ATCTGCCTGG AACAAAGAAC TGCACCTAAG CAGACCAGAA GCAAAATGTC
1351 TTCTTCACGG CATAAGGACA TCTCCACTTT TCTCTGTACC TGTGTGTATA
1401 GAAATAGATT AGAGCACAGT TGAAATTCAT GGAACTGGCA TTATTTAAGC
1451 AACTGGAATT CCACACTGTA GGAAGGTTTT GAAAATTGTT TGGTTGTAGA
1501 TTTTATCTTA TCCTTTAGTG TTGTGTTCCT ACTGTGATGT CTTGGTTTTT
1551 GTCATAGACT TAAGTTTATA AGTTTGAACT GGACTTGTTC GATTATAACC
1601 ACAAATTGTG TGTGTGTGTG TGTGTGTGTG TGTGTGTGTG TGTGTGTGTG
1651 TGTATGCCTG TGTGTATATA TAGAAGTCAT TATGGCAGAT GCACAGAAAT
1701 TGTGCAGTGA TGTAAATGTT CATACTTTAC AGAGCCTATA ATTTTTATTT
1751 TTCAATTTGT TTTTTCAAAA ATCTCTTCTC GGGGACAACA TCTGAAGGGT
1801 ATGTTGCATG CATTAAAAAA AATCATCTCA CATGCATTTT ATAGTTTTGG
1851 GGAAGAAAAT ATCATGGGGA GGTCTACCTT CAGTATCTTT AGTGCTTCTT
1901 ACCTGGTAAC TTGAGACTTT AAAAGAAGAA ACAAAGAGGG AAGATATGG
1951 GAGCGAATTT ATTCAAGAA TCTACAATGA CATTGAAGTT GTTGGAGGAA
2001 TGTACTGTAT TTAAAAAAAC CTTCTGTGAC ACATTCAAAA ATTTCATCTG
2051 AGCTGGATGC AGTGGCTTGT TCCTATAGTC CCAGCACTTT GGGAGGCTGA
2101 GGTGGGTGGA TTGCTTGAGC CCAGGAGTTG GAGACCAGTC TGGGAAACGT
2151 GGTGAGACCT CATCTCTACA AAATACAAAA AAATTAGCCG GGCATGGTGG
2201 CACGTGAGTG TAGTCTCAGC TACTCAGGAG GCTGAGATGA GAGGATCACT
2251 TGAGCCTGGG GAGGTCCAGG CCGCAGTGAT CCGAGATCAC ACCACTGCAT
2301 TCCAGCCTGG GTGACAGAGT GAGACCCTGT CCAAAAAAAA AAAAAAAAA
```

Figure 5 : B) SEQ ID NO: 4, nucleotide sequence of human PRKY cDNA

Length: 895 bp

```
  1  GGACCTGAGT GCCTCCCCAT GGAGGCGCCC GGGCCGGCCC AGGCGGCCGC
 51  GGCGGAGAGC AACTCCCGAG AGGTGACGGA GGATGCCGCC GACTGGGCGC
101  CCGCGCTCTG CCCCAGCCCC GAGGCGCGGT CGCCGGAGGC GCCTGCCTAC
151  CGCCTGCAGG ACTGCGACGC GCTGGTCACC ATGGGCACTG GGACGTTCGG
201  GCGGGTGCAC CTGGTGAAGG AGAAGACAGC CAAGCATTTC TTCGCCCTCA
251  AGGTGATGAG CATTCCCGAC GTCATCCGCC GGAAGCAGGA GCAGCACGTG
301  CACAATGAGA AGTCTGTCCT GAAGGAAGTC AGCCACCCGT TCCTCATCAG
351  GCTGTTCTGG ACGTGGCATG AGGAGCGCTT CCTCTACATG CTCATGGAGT
401  ATGTGCCGGG TGGCGAGCTC TTCAGCTACC TGCGCAACCG GGGCACTTC
451  TCCAGCACCA CGGGGCTCTT CTACTCTGCG GAGATCATCT GTGCCATTGA
501  GTACCTGCAC TCCAAGGAGA TCGTCTACAG GGATTTGAAG CCGGAGAACA
551  TCCTGCTGGA TAGGGATGGT CACATCAAGC TCACGGACTT TGGGTTTGCC
601  AAGAAGCTGG TAGACAGGAC TTGGACCCTC TGTGGAACAC CCGAGTACCT
651  AGCCCCCGAA GTCATTCAGA GCAAGGGCCA CGGAAGGGCC GTGGACTGGT
701  GGGCCCTCGG CATCCTGATA TTCGAGATGC TTTCGGGGTT TCCTCCATTT
751  TTTGATGACA ACCCGTTTGG CATTTATCAG AAAATTCTTG CAGGCAAACT
801  ATATTTCCCC AGACATTTGG ATTTCCATGT AAAAACGGGG CGAATGATGT
851  GAAACACCAT CGGTGGTTCC GCTCCGTGGA CTGGAAAGCT GTTCC
```

Figure 6 : A) SEQ ID NO: 5, coding nucleotide sequence of human PRKX cDNA

Length: 1077 bp

```
   1  ATGGAGGCGC CCGGGCTGGC CCAGGCGGCC GCGGCGGAGA GCGACTCCCG
  51  CAAGGTGGCG GAGGAGACCC CCGACGGGGC GCCCGCGCTC TGCCCCAGCC
 101  CTGAGGCGCT GTCGCCGGAG CCGCCTGTGT ACAGCCTGCA GGACTTTGAC
 151  ACGCTGGCCA CCGTGGGCAC TGGGACGTTC GGGCGGGTGC ACCTGGTGAA
 201  GGAGAAGACA GCCAAGCATT TCTTCGCCCT CAAGGTGATG AGCATTCCTG
 251  ACGTCATCCG CCTAAAGCAG GAGCAACACG TACACAATGA GAAGTCTGTC
 301  CTGAAGGAAG TCAGCCACCC GTTCCTCATC AGGCTGTTCT GGACGTGGCA
 351  TGACGAGCGC TTCCTCTACA TGCTCATGGA GTACGTGCCG GGCGGCGAGC
 401  TCTTCAGCTA CCTGCGCAAC CGGGGGCGCT TCTCCAGCAC CACGGGGCTC
 451  TTCTACTCTG CAGAGATCAT CTGTGCCATC GAGTACCTGC ACTCCAAAGA
 501  GATCGTCTAC AGGGACTTGA AGCCAGAGAA CATCCTGCTG GATAGGGATG
 551  GCCACATTAA GCTCACGGAC TTTGGGTTCG CCAAGAAGCT GGTAGACAGG
 601  ACTTGGACCC TCTGTGGAAC ACCCGAGTAC CTAGCCCCCG AAGTCATTCA
 651  GAGCAAGGGC CACGGAAGGG CCGTGGACTG GTGGGCCCTC GGCATCCTGA
 701  TATTCGAGAT GCTTTCGGGG TTTCCTCCGT TTTTTGATGA CAACCCGTTT
 751  GGCATTTATC AGAAAATTCT TGCAGGCAAA ATAGATTTCC CCAGACATTT
 801  GGATTTCCAT GTAAAAGACC TCATTAAGAA ACTGCTCGTG GTTGACAGAA
 851  CAAGGCGATT AGGAAACATG AAGAACGGGG CGAATGATGT GAAGCATCAT
 901  CGGTGGTTCC GCTCCGTGGA CTGGGAAGCT GTTCCGCAGA GAAAACTGAA
 951  GCCTCCCATC GTGCCCAAGA TAGCTGGTGA CGGCGACACT TCCAACTTCG
1001  AAACTTACCC TGAGAATGAC TGGGACACAG CCGCGCCCGT GCCGCAGAAG
1051  GATTTAGAAA TCTTCAAGAA TTTCTGA
```

Figure 6 : B) SEQ ID NO: 6, coding nucleotide sequence of human PRKY cDNA

Length: 834 bp

```
  1  ATGGAGGCGC CCGGGCCGGC CCAGGCGGCC GCGGCGGAGA GCAACTCCCG
 51  AGAGGTGACG GAGGATGCCG CCGACTGGGC GCCCGCGCTC TGCCCCAGCC
101  CCGAGGCGCG GTCGCCGGAG GCGCCTGCCT ACCGCCTGCA GGACTGCGAC
151  GCGCTGGTCA CCATGGGCAC TGGGACGTTC GGGCGGGTGC ACCTGGTGAA
201  GGAGAAGACA GCCAAGCATT TCTTCGCCCT CAAGGTGATG AGCATTCCCG
251  ACGTCATCCG CCGGAAGCAG GAGCAGCACG TGCACAATGA GAAGTCTGTC
301  CTGAAGGAAG TCAGCCACCC GTTCCTCATC AGGCTGTTCT GGACGTGGCA
351  TGAGGAGCGC TTCCTCTACA TGCTCATGGA GTATGTGCCG GGTGGCGAGC
401  TCTTCAGCTA CCTGCGCAAC CGGGGGCACT TCTCCAGCAC CACGGGGCTC
451  TTCTACTCTG CGGAGATCAT CTGTGCCATT GAGTACCTGC ACTCCAAGGA
501  GATCGTCTAC AGGGATTTGA AGCCGGAGAA CATCCTGCTG GATAGGGATG
551  GTCACATCAA GCTCACGGAC TTTGGGTTTG CCAAGAAGCT GGTAGACAGG
601  ACTTGGACCC TCTGTGGAAC ACCCGAGTAC CTAGCCCCCG AAGTCATTCA
651  GAGCAAGGGC CACGGAAGGG CCGTGGACTG GTGGGCCCTC GGCATCCTGA
701  TATTCGAGAT GCTTTCGGGG TTTCCTCCAT TTTTTGATGA CAACCCGTTT
751  GGCATTTATC AGAAAATTCT TGCAGGCAAA CTATATTTCC CCAGACATTT
801  GGATTTCCAT GTAAAAACGG GGCGAATGAT GTGA
```

Figure 7: Alignment of PRKX RT-PCR primers SEQ ID NO: 7 and SEQ ID NO: 8 with human PRKX cDNA, SEQ ID NO: 3

```
SEQ ID NO:7 (PRIMER A)        1 TGGGGAGGTCTACCTTCAGTATC    1
                                |||||||||||||||||||||||
SEQ ID NO:3                1865 TGGGGAGGTCTACCTTCAGTATC 1887

SEQ ID NO:8 (PRIMER B)       21 GGGAAGATATGGGAGCGAATT    1
                                |||||||||||||||||||||
SEQ ID NO:3                1939 GGGAAGATATGGGAGCGAATT 1959
```

Figure 8: Schematic alignment of SEQ ID NO: 3, SEQ ID NO: 5, and RT-PCR primer sequences of PRKX
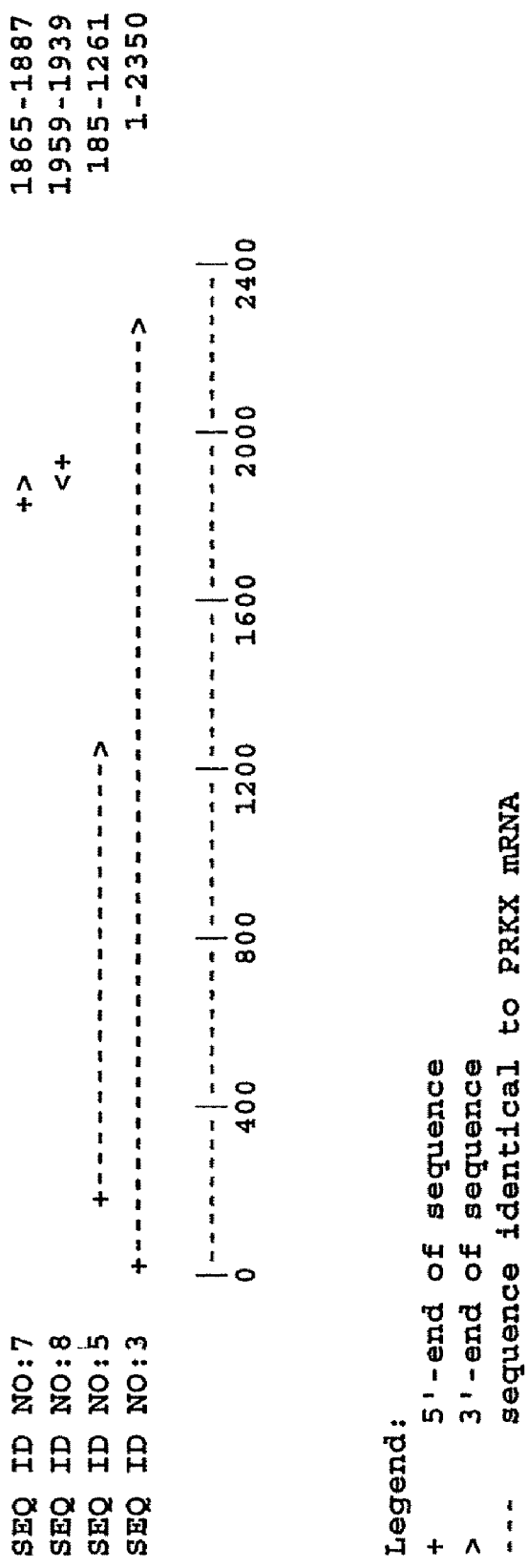
```
SEQ ID NO:7                                    1865-1887
SEQ ID NO:8                                    1959-1939
SEQ ID NO:5                                     185-1261
SEQ ID NO:3                                       1-2350
```
Legend:
+     5'-end of sequence
>     3'-end of sequence
- - - sequence identical to PRKX mRNA Co-deposition of PRKX protein with amyloid plaques is detected in the cerebral cortex of AD patients, but is absent from controls Expression by astrocytes of PRKX protein is strongly enhanced in the cerebral cortex of AD patients as compared to controls PRKX protein expression is associated with plaque-associated microglial and astrocytic inflammation, which is absent from controls

Figure 12:
LightCycler analysis of pka-C3 expression of flies expressing pka-C3 (02687) and pka-C3 (03065) under the control of GMR-Gal4 in the adult complex eye

| name | pka-C3 cycle number | pka-C3 mean | pka-C3 stdv | rp49 cycle number | rp49 mean | rp49 stdv | rp49 factor | mean pka-C3 x factor rp49 | difference | expression normalized to housekeeping gene (rp49) and efficiency (E) of pka-C3 primer |
|---|---|---|---|---|---|---|---|---|---|---|
| GMR-GAL4 | 26,22 | 26,360 | 0,1212 | 20 | 20,087 | 0,0757 | 1,000 | 26,36 | 0,000 | 1,000 |
| GMR-GAL4 | 26,43 | | | 20,12 | | | | | | |
| GMR-GAL4 | 26,43 | | | 20,14 | | | | | | |
| | | | | | | | | | | |
| pka-C3 (02687) | 26,92 | 26,930 | 0,0656 | 20,03 | 20,013 | 0,0208 | 1,003664 | 27,0286775 | -0,669 | 0,660363020034636 |
| pka-C3 (02687) | 26,87 | | | 20,02 | | | | | | |
| pka-C3 (02687) | 27,00 | | | 19,99 | | | | | | |
| | | | | | | | | | | |
| pka-C3 (03065) | 24,56 | 24,610 | 0,0436 | 19,95 | 19,950 | 0,0800 | 1,00685 | 24,7785898 | 1,5814102 | 2,668151692 |
| pka-C3 (03065) | 24,63 | | | 20,03 | | | | | 2,2500877 | 4,040431718 |
| pka-C3 (03065) | 24,64 | | | 19,87 | | | | | | |

$E = 10^{(-1/slope)}$  slope = -3,724  $E = 1,86$  pka-C3 primer pair

Co-expression of Drosophila pka-C3 (03065) accelerates a TauP301L induced degenerative eye-phenotype in young flies whereas a knock-down of pka-C3 (02687) function has no impact on photoreceptor cell degeneration Phosphorylation of Ser214 of TauP301L in flies co-expressing TauP301L and pka-C3 (02687) or pka-C3 (03065)

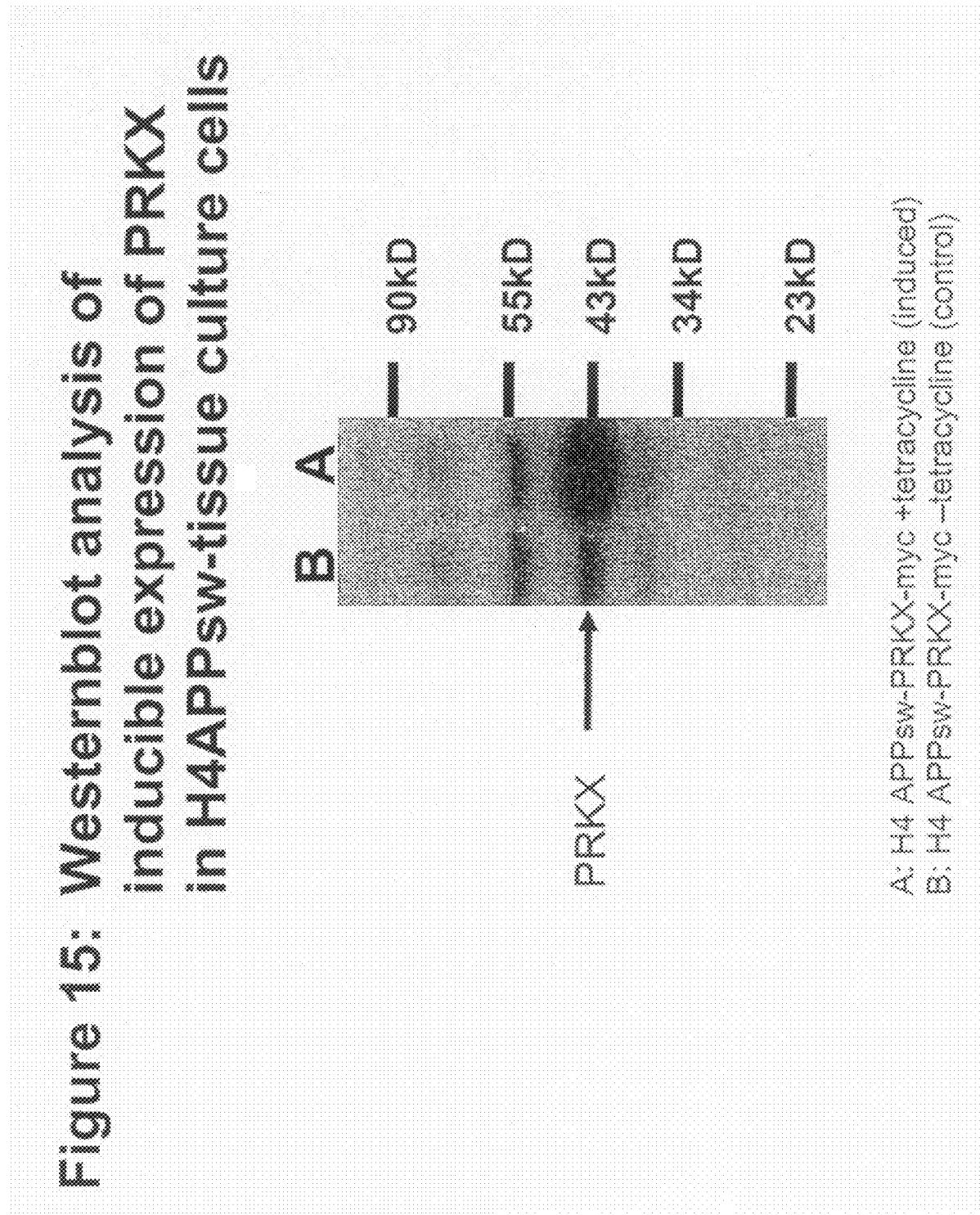

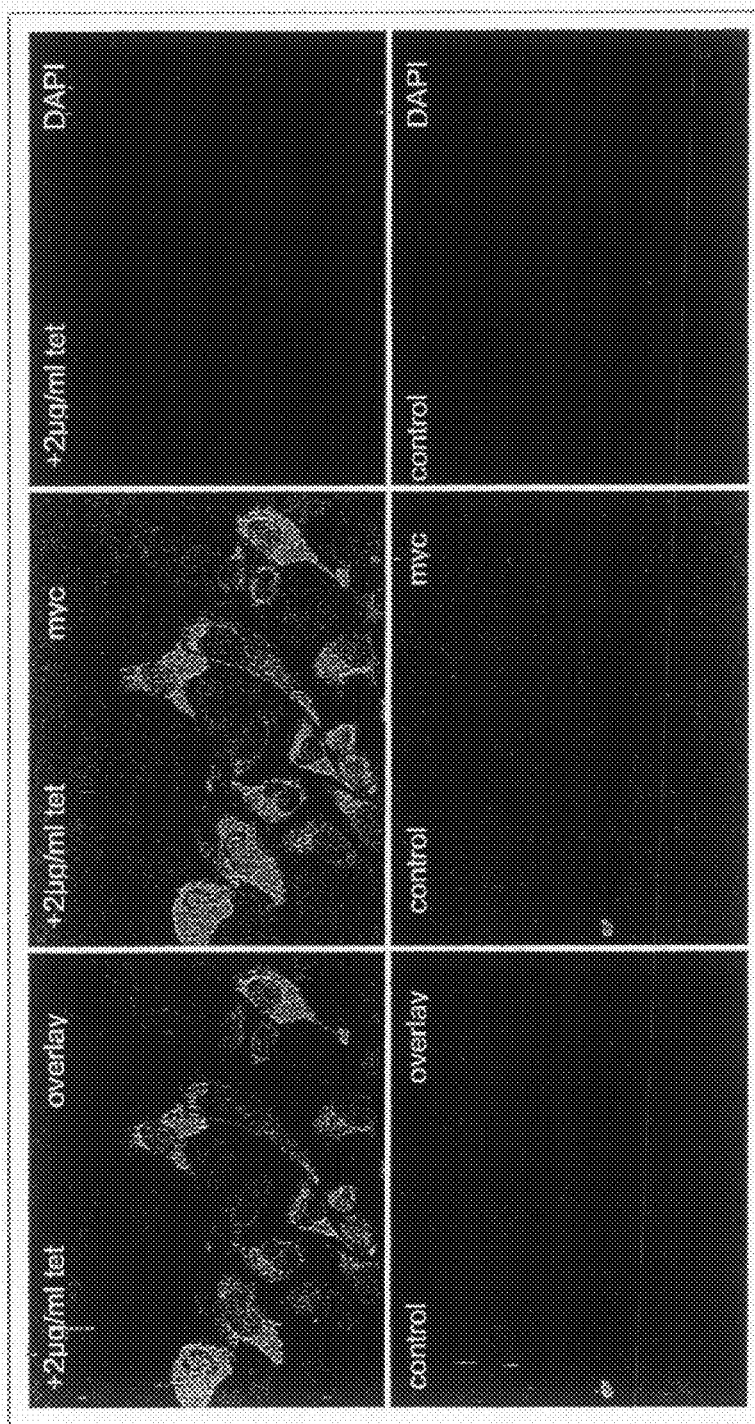
Figure 16: Immunofluorescence analysis of inducible expression of PRKX in H4APPsw-tissue culture cells

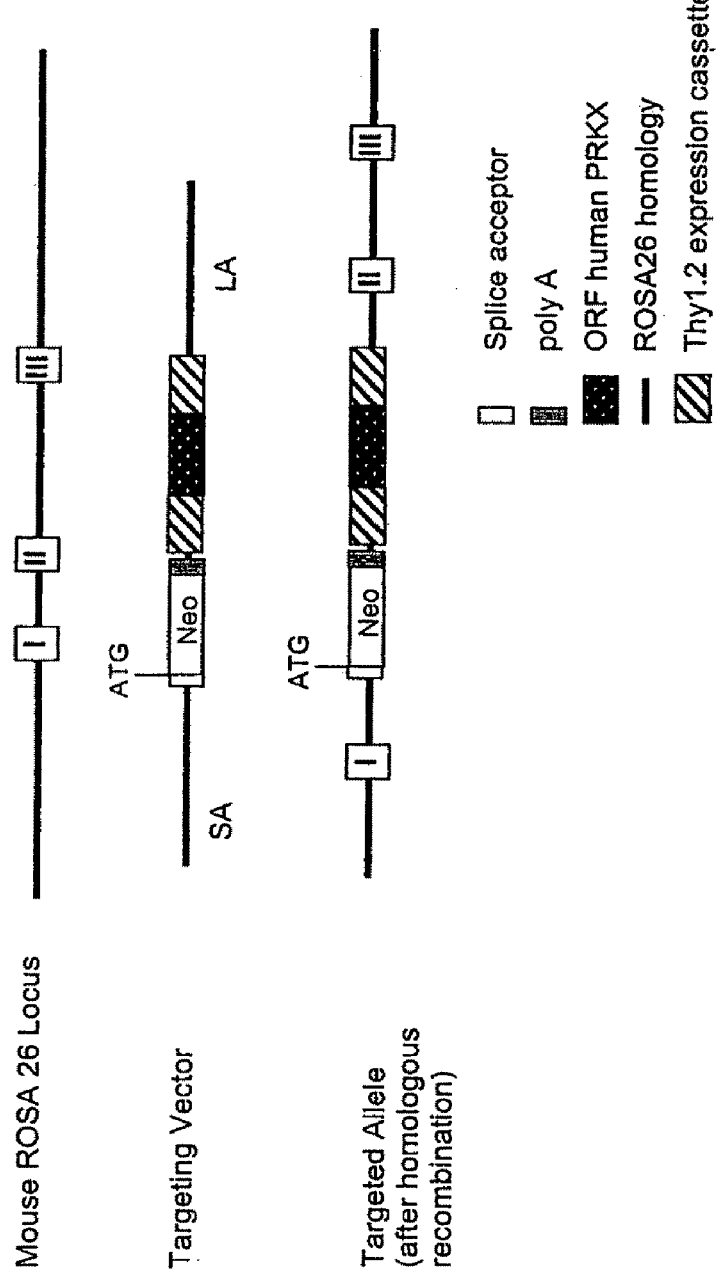
Figure 17: Targeting strategy for transgenic mice expressing human PRKX in neurons

SEQUENCE LISTING

<160> NUMBER OF SEQ ID NOS: 6

<210> SEQ ID NO 1
<211> LENGTH: 358
<212> TYPE: PRT
<213> ORGANISM: Homo Sapiens

<400> SEQUENCE: 1

```
Met Glu Ala Pro Gly Leu Ala Gln Ala Ala Ala Glu Ser Asp Ser
 1               5                  10                  15

Arg Lys Val Ala Glu Thr Pro Asp Gly Ala Pro Ala Leu Cys Pro
                20                  25                  30

Ser Pro Glu Ala Leu Ser Pro Glu Pro Pro Val Tyr Ser Leu Gln Asp
                35                  40                  45

Phe Asp Thr Leu Ala Thr Val Gly Thr Gly Thr Phe Gly Arg Val His
 50                      55                  60

Leu Val Lys Glu Lys Thr Ala Lys His Phe Phe Ala Leu Lys Val Met
 65                      70                  75                  80

Ser Ile Pro Asp Val Ile Arg Leu Lys Gln Glu Gln His Val His Asn
                85                  90                  95

Glu Lys Ser Val Leu Lys Glu Val Ser His Pro Phe Leu Ile Arg Leu
                100                 105                 110

Phe Trp Thr Trp His Asp Glu Arg Phe Leu Tyr Met Leu Met Glu Tyr
                115                 120                 125

Val Pro Gly Gly Glu Leu Phe Ser Tyr Leu Arg Asn Arg Gly Arg Phe
                130                 135                 140

Ser Ser Thr Thr Gly Leu Phe Tyr Ser Ala Glu Ile Ile Cys Ala Ile
145                     150                 155                 160

Glu Tyr Leu His Ser Lys Glu Ile Val Tyr Arg Asp Leu Lys Pro Glu
                165                 170                 175

Asn Ile Leu Leu Asp Arg Asp Gly His Ile Lys Leu Thr Asp Phe Gly
                180                 185                 190

Phe Ala Lys Lys Leu Val Asp Arg Thr Trp Thr Leu Cys Gly Thr Pro
                195                 200                 205

Glu Tyr Leu Ala Pro Glu Val Ile Gln Ser Lys Gly His Gly Arg Ala
                210                 215                 220

Val Asp Trp Trp Ala Leu Gly Ile Leu Ile Phe Glu Met Leu Ser Gly
225                     230                 235                 240

Phe Pro Pro Phe Phe Asp Asp Asn Pro Phe Gly Ile Tyr Gln Lys Ile
                245                 250                 255

Leu Ala Gly Lys Ile Asp Phe Pro Arg His Leu Asp Phe His Val Lys
                260                 265                 270

Asp Leu Ile Lys Lys Leu Leu Val Asp Arg Thr Arg Arg Leu Gly
                275                 280                 285

Asn Met Lys Asn Gly Ala Asn Asp Val Lys His His Arg Trp Phe Arg
                290                 295                 300

Ser Val Asp Trp Glu Ala Val Pro Gln Arg Lys Leu Lys Pro Pro Ile
305                     310                 315                 320

Val Pro Lys Ile Ala Gly Asp Gly Asp Thr Ser Asn Phe Glu Thr Tyr
                325                 330                 335

Pro Glu Asn Asp Trp Asp Thr Ala Ala Pro Val Pro Gln Lys Asp Leu
                340                 345                 350

Glu Ile Phe Lys Asn Phe
                355
```

<210> SEQ ID NO 2
<211> LENGTH: 277
<212> TYPE: PRT
<213> ORGANISM: Homo Sapiens

<400> SEQUENCE: 2

```
Met Glu Ala Pro Gly Pro Ala Gln Ala Ala Ala Glu Ser Asn Ser
1               5                   10                  15

Arg Glu Val Thr Glu Asp Ala Ala Asp Trp Ala Pro Ala Leu Cys Pro
                20                  25                  30

Ser Pro Glu Ala Arg Ser Pro Glu Ala Pro Ala Tyr Arg Leu Gln Asp
            35                  40                  45

Cys Asp Ala Leu Val Thr Met Gly Thr Gly Thr Phe Gly Arg Val His
    50                  55                  60

Leu Val Lys Glu Lys Thr Ala Lys His Phe Phe Ala Leu Lys Val Met
65                  70                  75                  80

Ser Ile Pro Asp Val Ile Arg Arg Lys Gln Glu Gln His Val His Asn
                85                  90                  95

Glu Lys Ser Val Leu Lys Glu Val Ser His Pro Phe Leu Ile Arg Leu
            100                 105                 110

Phe Trp Thr Trp His Glu Glu Arg Phe Leu Tyr Met Leu Met Glu Tyr
        115                 120                 125

Val Pro Gly Gly Glu Leu Phe Ser Tyr Leu Arg Asn Arg Gly His Phe
    130                 135                 140

Ser Ser Thr Thr Gly Leu Phe Tyr Ser Ala Glu Ile Ile Cys Ala Ile
145                 150                 155                 160

Glu Tyr Leu His Ser Lys Glu Ile Val Tyr Arg Asp Leu Lys Pro Glu
                165                 170                 175

Asn Ile Leu Leu Asp Arg Asp Gly His Ile Lys Leu Thr Asp Phe Gly
            180                 185                 190

Phe Ala Lys Lys Leu Val Asp Arg Thr Trp Thr Leu Cys Gly Thr Pro
        195                 200                 205

Glu Tyr Leu Ala Pro Glu Val Ile Gln Ser Lys Gly His Gly Arg Ala
    210                 215                 220

Val Asp Trp Trp Ala Leu Gly Ile Leu Ile Phe Glu Met Leu Ser Gly
225                 230                 235                 240

Phe Pro Pro Phe Phe Asp Asp Asn Pro Phe Gly Ile Tyr Gln Lys Ile
                245                 250                 255

Leu Ala Gly Lys Leu Tyr Phe Pro Arg His Leu Asp Phe His Val Lys
            260                 265                 270

Thr Gly Arg Met Met
        275
```

<210> SEQ ID NO 3
<211> LENGTH: 2350
<212> TYPE: DNA
<213> ORGANISM: Homo Sapiens

<400> SEQUENCE: 3

```
gccgcccagc cattgtcccc gtcgctccgt cagccgcgcc ggaccgcgca ccaggaggcg      60
agagcgcgca tggggagcct ctgttgatgc cgccgccgcg ccgccctccg aggctgcgtc     120
ccgggaagcc cggctccccg agcgctccgg cctggcccgg tgccccggac ctgagtgcgt     180
ccccatggag gcgcccgggc tggcccaggc ggccgcggcg gagagcgact cccgcaaggt     240
ggcggaggag accccgacg gggcgcccgc gctctgcccc agccctgagg cgctgtcgcc     300
```

```
ggagccgcct gtgtacagcc tgcaggactt tgacacgctg gccaccgtgg gcactgggac      360
gttcgggcgg gtgcacctgg tgaaggagaa gacagccaag catttcttcg ccctcaaggt      420
gatgagcatt cctgacgtca tccgcctaaa gcaggagcaa cacgtacaca atgagaagtc      480
tgtcctgaag gaagtcagcc acccgttcct catcaggctg ttctggacgt ggcatgacga      540
gcgcttcctc tacatgctca tggagtacgt gccgggcggc gagctcttca gctacctgcg      600
caaccggggg cgcttctcca gcaccacggg gctcttctac tctgcagaga tcatctgtgc      660
catcgagtac ctgcactcca agagatcgt ctacagggac ttgaagccag agaacatcct      720
gctggatagg gatggccaca ttaagctcac ggactttggg ttcgccaaga agctggtaga      780
caggacttgg accctctgtg aacacccga gtacctagcc cccgaagtca ttcagagcaa      840
gggccacgga agggccgtgg actggtgggc cctcggcatc ctgatattcg agatgctttc      900
ggggtttcct ccgttttttg atgacaaccc gtttggcatt tatcagaaaa ttcttgcagg      960
caaaatagat ttccccagac atttggattt ccatgtaaaa gacctcatta agaaactgct      1020
cgtggttgac agaacaaggc gattaggaaa catgaagaac ggggcgaatg atgtgaagca      1080
tcatcggtgg ttccgctccg tggactggga agctgttccg cagagaaaac tgaagcctcc      1140
catcgtgccc aagatagctg gtgacggcga cacttccaac ttcgaaactt accctgagaa      1200
tgactgggac acagccgcgc ccgtgccgca aaggattta aaatcttca agaatttctg      1260 aggacaggag ctcacatctg aagaaacag aagattgga atctgcctgg aacaaagaac      1320
tgcacctaag cagaccagaa gcaaaatgtc ttcttcacgg cataaggaca tctccacttt      1380
tctctgtacc tgtgtgtata gaaatagatt agagcacagt tgaaattcat ggaactggca      1440
ttatttaagc aactggaatt ccacactgta ggaaggtttt gaaaattgtt tggttgtaga      1500
ttttatctta tccttttagtg ttgtgttcct actgtgatgt cttggttttt gtcatagact      1560 taagttata gttgaact ggacttgttc gattataacc acaaattgtg tgtgtgtgtg      1620
tgtgtgtgtg tgtgtgtgtg tgtgtgtgtg tgtatgcctg tgtgtatata tagaagtcat      1680 tatgcagat gcacagaaat tgtgcagtga tgtaaatgtt catactttac agagcctata      1740
atttttattt ttcaatttgt ttttcaaaa atctcttctc ggggacaaca tctgaagggt      1800
atgttgcatg cattaaaaaa aatcatctca catgcatttt atagtttggg ggaagaaat       1860 atcatgggga ggtctaccct cagtatctttt agtgcttctt acctggtaac ttgagacttt      1920
aaaagaagaa acaaagaggg gaagatatgg gagcgaattt attccaagaa tctacaatga      1980
cattgaagtt gttggaggaa tgtactgtat ttaaaaaaac cttctgtgac acattcaaaa      2040
atttcatctg agctggatgc agtggcttgt tcctatagtc ccagcacttt gggaggctga      2100
ggtgggtgga ttgcttgagc ccaggagttg agaccagtc tgggaaacgt ggtgagacct      2160
catctctaca aaatacaaaa aaattagccg gcatggtgg cacgtgagtg tagtctcagc      2220
tactcaggag gctgagatga gaggatcact tgagcctggg gaggtccagg ccgcagtgat      2280
ccgagatcac accactgcat tccagcctgg gtgacagagt gagaccctgt ccaaaaaaaa      2340
aaaaaaaaaa                                                            2350

<210> SEQ ID NO 4
<211> LENGTH: 895
<212> TYPE: DNA
<213> ORGANISM: Homo Sapiens

<400> SEQUENCE: 4
ggacctgagt gcctccccat ggaggcgccc gggccggccc aggcggccgc ggcggagagc        60
```

```
aactcccgag aggtgacgga ggatgccgcc gactgggcgc ccgcgctctg ccccagcccc    120
gaggcgcggt cgccggaggc gcctgcctac cgcctgcagg actgcgacgc gctggtcacc    180
atgggcactg ggacgttcgg gcgggtgcac ctggtgaagg agaagacagc caagcatttc    240
ttcgccctca aggtgatgag cattcccgac gtcatccgcc ggaagcagga gcagcacgtg    300
cacaatgaga agtctgtcct gaaggaagtc agccacccgt tcctcatcag gctgttctgg    360
acgtggcatg aggagcgctt cctctacatg ctcatggagt atgtgccggg tggcgagctc    420
ttcagctacc tgcgcaaccg ggggcacttc tccagcacca cggggctctt ctactctgcg    480
gagatcatct gtgccattga gtacctgcac tccaaggaga tcgtctacag ggatttgaag    540
ccggagaaca tcctgctgga tagggatggt cacatcaagc tcacggactt tgggtttgcc    600
aagaagctgg tagacaggac ttggaccctc tgtggaacac ccgagtacct agcccccgaa    660
gtcattcaga gcaagggcca cggaagggcg tggactggt gggccctcgg catcctgata    720
ttcgagatgc tttcggggtt tcctccattt tttgatgaca cccgtttgg catttatcag    780 aaaattcttg caggcaaact atatttcccc agacatttgg atttccatgt aaaaacgggg    840
cgaatgatgt gaaacaccat cggtggttcc gctccgtgga ctggaaagct gttcc         895

<210> SEQ ID NO 5
<211> LENGTH: 1077
<212> TYPE: DNA
<213> ORGANISM: Homo Sapiens

<400> SEQUENCE: 5
atggaggcgc ccgggctggc ccaggcggcc gcggcggaga gcgactcccg caaggtggcg     60
gaggagaccc ccgacggggc gcccgcgctc tgccccagcc ctgaggcgct gtcgccggag    120
ccgcctgtgt acagcctgca ggactttgac acgctggcca ccgtgggcac tgggacgttc    180
gggcgggtgc acctggtgaa ggagaagaca gccaagcatt tcttcgccct caaggtgatg    240
agcattcctg acgtcatccg cctaaagcag gagcaacacg tacacaatga agagtctgtc    300
ctgaaggaag tcagccaccc gttcctcatc aggctgttct ggacgtggca tgacgagcgc    360
ttcctctaca tgctcatgga gtacgtgccg gcggcgagc tcttcagcta cctgcgcaac    420
cgggggcgct tctccagcac cacggggctc ttctactctg cagagatcat ctgtgccatc    480
gagtacctgc actccaaaga gatcgtctac agggacttga agccagagaa catcctgctg    540
gatagggatg ccacattaa gctcacggac tttgggttcg ccaagaagct ggtagacagg    600
acttggaccc tctgtggaac acccgagtac ctagcccccg aagtcattca gagcaagggc    660
cacggaaggg ccgtggactg gtgggccctc ggcatcctga tattcgagat gctttcgggg    720
tttcctccgt tttttgatga caacccgttt ggcatttatc agaaaattct tgcaggcaaa    780
atagatttcc ccagacattt ggatttccat gtaaaagacc tcattaagaa actgctcgtg    840
gttgacagaa caaggcgatt aggaaacatg aagaacgggg cgaatgatgt gaagcatcat    900
cggtggttcc gctccgtgga ctggaaagct gttccgcaga aaaactgaa gcctcccatc    960 gtgcccaaga tagctggtga cggcgacact tccaacttcg aaacttaccc tgagaatgac   1020
tgggacacag ccgcgcccgt gccgcagaag gatttagaaa tcttcaagaa tttctga     1077

<210> SEQ ID NO 6
<211> LENGTH: 834
<212> TYPE: DNA
<213> ORGANISM: Homo Sapiens

<400> SEQUENCE: 6
```

```
atggaggcgc ccgggccggc ccaggcggcc gcggcggaga gcaactcccg agaggtgacg    60
gaggatgccg ccgactgggc gcccgcgctc tgccccagcc ccgaggcgcg gtcgccggag   120
gcgcctgcct accgcctgca ggactgcgac gcgctggtca ccatgggcac tgggacgttc   180
gggcgggtgc acctggtgaa ggagaagaca gccaagcatt tcttcgccct caaggtgatg   240
agcattcccg acgtcatccg ccggaagcag gagcagcacg tgcacaatga gaagtctgtc   300
ctgaaggaag tcagccaccc gttcctcatc aggctgttct ggacgtggca tgaggagcgc   360
ttcctctaca tgctcatgga gtatgtgccg ggtggcgagc tcttcagcta cctgcgcaac   420
cgggggcact tctccagcac cacggggctc ttctactctg cggagatcat ctgtgccatt   480
gagtacctgc actccaagga gatcgtctac agggatttga agccggagaa catcctgctg   540
gatagggatg gtcacatcaa gctcacggac tttgggtttg ccaagaagct ggtagacagg   600
acttggaccc tctgtggaac acccgagtac ctagccccg aagtcattca gagcaagggc   660
cacggaaggg ccgtggactg gtgggccctc ggcatcctga tattcgagat gctttcgggg   720
tttcctccat tttttgatga caacccgttt ggcatttatc agaaaattct tgcaggcaaa   780
ctatatttcc ccagacattt ggatttccat gtaaaaacgg ggcgaatgat gtga         834
```

DIAGNOSTIC AND THERAPEUTIC TARGET PRKX PROTEINS FOR NEURODEGENERATIVE DISEASES

This application is a U.S. national stage of International Application No. PCT/EP2006/062741 filed May 30, 2006.

The present invention relates to methods of diagnosing, prognosticating and monitoring the progression of neurodegenerative diseases in a subject. Furthermore, methods of therapy control and screening for modulating agents of neurodegenerative diseases are provided. The invention also discloses pharmaceutical compositions, kits, and recombinant animal models.

Neurodegenerative diseases, in particular Alzheimer's disease (AD), have a strongly debilitating impact on a patient's life. Furthermore, these diseases constitute an enormous health, social, and economic burden. AD is the most common neurodegenerative disease, accounting for about 70% of all dementia cases, and it is probably the most devastating age-related neurodegenerative condition affecting about 10% of the population over 65 years of age and up to 45% over age 85 (Vickers et al., *Progress in Neurobiology* 2000, 60: 139-165; Walsh and Selkoe, *Neuron* 2004, 44:181-193). Presently, this amounts to an estimated 12 million cases in the US, Europe, and Japan. This situation will inevitably worsen with the demographic increase in the number of old people in developed countries. The neuropathological hallmarks that occur in the brains of individuals with AD are senile plaques, composed of amyloid-β protein, and profound cytoskeletal changes coinciding with the appearance of abnormal filamentous structures and the formation of neurofibrillary tangles.

The amyloid-β protein evolves from the cleavage of the amyloid precursor protein (APP) by different kinds of proteases (Selkoe and Kopan, *Annu Rev Neurosci* 2003, 26:565-597; Ling et al., *Int J Biochem Cell Biol* 2003, 35:1505-1535). Two types of plaques, diffuse plaques and neuritic plaques can be detected in the brain of AD patients. They are primarily found in the cerebral cortex and hippocampus. The generation of toxic Aβ deposits in the brain starts very early in the course of AD, and it is discussed to be a key player for the subsequent destructive processes leading to AD pathology. The other pathological hallmarks of AD are neurofibrillary tangles (NFTs) and abnormal neurites, described as neuropil threads (Braak and Braak, *J Neural Transm* 1998, 53: 127-140). NFTs emerge inside neurons and consist of chemically altered tau, which forms paired helical filaments (PHF) twisted around each other. Characteristically for AD the microtubule associated protein tau aggregating in paired helical filaments displays the abnormal phosphorylation of certain amino acid positions, including among others Ser214. The pattern of tau phosphorylation seems to correlate with the loss of neuronal integrity and along the formation of NFTs, a loss of neurons can be observed (Johnson and Jenkins, *J Alzheimers Dis* 1996, 1: 38-58; Johnson and Hartigan, *J Alzheimers Dis* 1999, 1: 329-351). The appearance of neurofibrillary tangles and their increasing number correlates well with the clinical severity of AD (Schmitt et al., *Neurology* 2000, 55: 370-376). AD is a progressive disease that is associated with early deficits in memory formation and ultimately leads to the complete erosion of higher cognitive function. The cognitive disturbances include among other things memory impairment, aphasia, agnosia and the loss of executive functioning. A characteristic feature of the pathogenesis of AD is the selective vulnerability of particular brain regions and subpopulations of nerve cells to the degenerative process. Specifically, the inferior temporal lobe region and the hippocampus are affected early and more severely during the progression of the disease. On the other hand, neurons within the frontal cortex, occipital cortex, and the cerebellum remain largely intact and are protected from neurodegeneration (Terry et al., *Annals of Neurology* 1981, 10: 184-92).

Currently, there is no cure for AD, nor is there an effective treatment to halt the progression of AD or even to diagnose AD ante-mortem with high probability. Several risk factors have been identified that predispose an individual to develop AD, among them most prominently the epsilon 4 allele of the three different existing alleles (epsilon 2, 3, and 4) of the apolipoprotein E gene (ApoE) (Strittmatter et al., *Proc Natl Acad Sci USA* 1993, 90: 1977-81; Roses, *Ann NY Acad Sci* 1998, 855: 738-43). Although there are rare examples of early-onset AD which have been attributed to genetic defects in the genes for amyloid precursor protein (APP) on chromosome 21, presenilin-1 on chromosome 14, and presenilin-2 on chromosome 1, the prevalent form of late-onset sporadic AD is of hitherto unknown etiologic origin. The late onset and complex pathogenesis of neurodegenerative disorders pose a formidable challenge to the development of therapeutic and diagnostic agents. It is crucial to expand the pool of potential drug targets and diagnostic markers.

It is therefore an object of the present invention to provide insight into the pathogenesis of neurological diseases and to provide methods, materials, agents, compositions, and animal models which are suited inter alia for the diagnosis and development of a treatment of these diseases. This object has been solved by the features of the independent claims. The subclaims define preferred embodiments of the present invention.

The present invention is based on the finding of the association of PRKX with neurodegenerative diseases, in particular Alzheimer's disease. The PRKX gene, which was identified in studies designed to elucidate signaling pathways in renal epithelial morphogenesis, is coding for a cAMP-dependent serine/threonine kinase. This gene was found as an interesting candidate regulatory gene, because it was activated transcriptionally in fetal kidneys during organogenesis. The PRKX gene which is located on the X chromosome at Xp22.3 (Klink et al., *Hum. Mol. Genet.* 1995, 4: 869-878; Schiebel et al., *Hum. Mol. Genet.* 1997, 6:1985-1989) has a homologue (PRKY) on the Y chromosome. Both PRKX and PRKY genes represent members of the cAMP-dependent serine threonine protein kinase gene family. The unprecedented high sequence identity (95% at cDNA level) and identical orientation of PRKX to its homologue on the Y chromosome, PRKY, explains the high frequency of abnormal pairing and subsequent ectopic recombination between the specific regions on the X and Y chromosomes. Due to this fact PRKY may be regarded herein as a member of the PRKX family.

Previous studies have demonstrated functional differences between protein kinase X (PRKX) and protein kinase A (PKA) kinases (Zimmermann et al., *J. Biol. Chem.* 1999, 274: 5370-5378) and implicated PRKX in granulocyte/macrophage lineage differentiation (Semizarov et al., *Proc. Natl. Acad. Sci. USA* 95 1998, 15412-15417) suggesting that PRKX may have important developmental functions. PRKX is involved in myeloid cell maturation and ureteric bud development and is up-regulated in autosomal dominant polycystic kidney disease. Gene recombination with PRKX causes Swyer's syndrome. PRKX overexpression activates migration of cultured renal epithelial cells in presence of cAMP (Li et al., *PNAS* 2002, 99: 9260-9265). PRKX possess 50% identity on protein level to cAMP-dependent protein kinase A, catalytic subunit, isoforms alpha and beta, which are the closest human homologs of the PRKX family. Because the catalytic domain of PRKX shares greater amino acid homology with the *Dictyostelium* and *Drosophila* kinase genes KAPC-DICDI and DC2 than with mammalian PKA genes (Mann et al., *Proc. Natl. Acad. Sci. USA* 1992, 89: 10701-10705; Anjard et al., *Biochemistry* 1993, 32: 9532-9538; Melendez et al., *Genetics* 1995, 141: 1507-1520; Kalderon et al., *Genes Dev.* 1988, 2: 1539-1556), it is plausible that PRKX and KAPC-DICDI might share unique functions not conserved in PKA genes. KAPC-DICDI plays an important role in the development of *Dictyostelium discoideum*, notably in morphogenetic cell migration (Mann et al., *Dev. Biol.* 1997, 183: 208-221; Harwood et al., *Dev. Biol.* 1992, 149: 90-99) as well as in transcriptional regulation of cellular differentiation (Primpke et al., *Dev. Biol.* 2000, 221: 101-111; Aubry et al., *Annu. Rev. Cell Dev. Biol.* 1999, 15: 469-517), implying that PRKX also might regulate morphogenesis in higher eukaryotes in addition to its proposed role in regulating cellular differentiation in hematopoietic lineages. Phylogenetic analysis showed that PRKX, KAPC-DICDI, DC2, *Ascaris suum* KAPC ASCU, and *Caenorhabditis elegans* kin-1/CAB41352 kinases comprise an ancient gene family distinct from the PKA, PKB, PKC, SGK, or PKG kinase gene families. It was found that expression of the PRKX kinase, but not the PKA kinase, strongly activated cellular morphogenesis and drove the formation of epithelial tubular structures in vitro associated with a stimulation of cellular migration. PRKX kinase might therefore regulate tubulogenesis during kidney development and the PRKX gene family may play an important function in cellular morphogenesis in multicellular eukaryotes. A relation of PRKX with neurodegenerative diseases, in particular Alzheimer's disease has not been disclosed so far.

BRIEF DESCRIPTION OF THE DRAWINGS

FIG. 2 lists the data for the verification of differences in the levels of PRKX gene derived mRNA in human brain tissue samples from individuals corresponding to different Braak stages indicative for AD as measured by quantitative RT-PCR analysis.

FIG. 3 shows the analysis of absolute levels of PRKX gene derived mRNA in human brain tissue samples from individuals corresponding to different Braak stages indicative for AD as measured by quantitative RT-PCR and using statistical method of the median at 98%-confidence level.

FIG. 4A discloses SEQ ID NO: 1, the amino acid sequence of the human PRKX protein.

FIG. 4B discloses SEQ ID NO: 2, the amino acid sequence of the human PRKY protein.

FIG. 5A shows SEQ ID NO: 3, the nucleotide sequence of the human PRKX cDNA.

FIG. 5B shows SEQ ID NO: 4, the nucleotide sequence of the human PRKY cDNA.

FIG. 6A depicts SEQ ID NO: 5, the coding sequence (cds) of the human PRKX gene.

FIG. 6B depicts SEQ ID NO: 6, the coding sequence (cds) of the human PRKY gene.

FIG. 7 depicts the sequence alignment of the primers used for measuring levels of PRKX gene derived mRNA by quantitative RT-PCR with the corresponding clippings of PRKX cDNA.

FIG. 8 schematically charts the alignment of the PRKX cDNA sequence, the coding sequence and both primer sequences used for PRKX transcription level profiling.

FIG. 12 shows the detection of Drosophila pka-C3 (ortholog of the human PRKX gene) mRNA expression in two different pka-C3 transgenic fly lines.

FIG. 15 shows Western blot analysis of inducible PRKX protein production in H4-neuroglioma cells stably co-expressing the Swedish Mutant APP.

FIG. 16 shows the immunofluorescence analysis of inducible PRKX protein production in H4-neuroglioma cells stably co-expressing the Swedish Mutant APP.

FIG. 17 depicts the targeting strategy for transgenic mice expressing the human PRKX gene in neurons.

Figure 1:
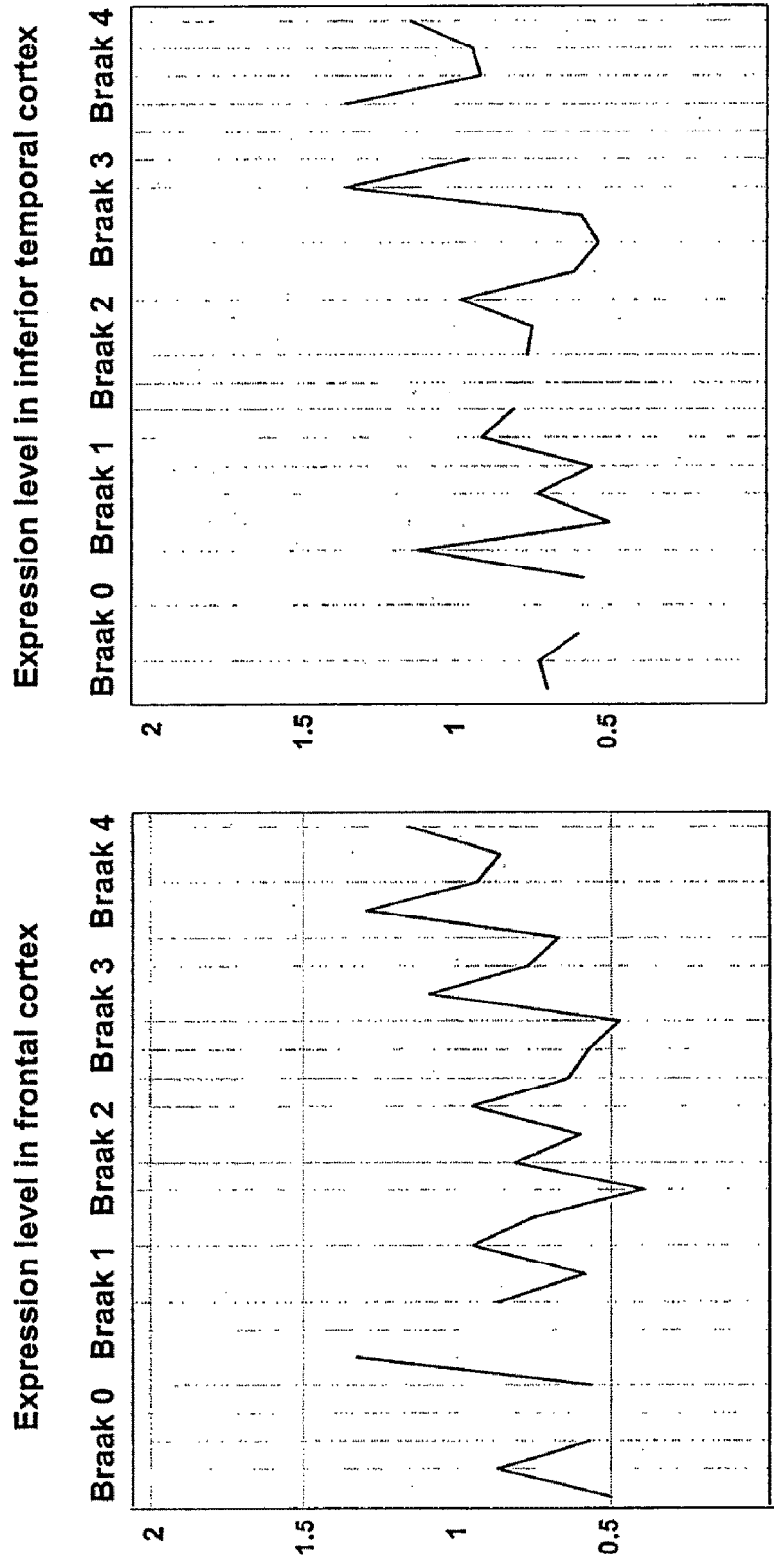
FIG. 1 discloses the identification of differences in the levels of PRKX gene derived mRNA in human brain tissue samples from individuals corresponding to different Braak stages as measured and compared by GeneChip analyses. It indicates that the levels of the respective mRNA species correlate quantitatively with AD progression and thus are indicative for AD as measured by the neuropathological staging of brain tissue samples according to Braak and Braak (Braak staging).

The singular forms "a", "an", and "the" as used herein and in the claims include plural reference unless the context dictates otherwise. For example, "a cell" means as well a plurality of cells, and so forth.

The term "and/or" as used in the present specification and in the claims implies that the phrases before and after this term are to be considered either as alternatives or in combination. For instance, the wording "determination of a level and/or an activity" means that either only a level, or only an activity, or both a level and an activity are determined.

The term "level" as used herein is meant to comprise a gage of, or a measure of the amount of, or a concentration of a substance such as a transcription product, for instance an mRNA, or a translation product, for instance a protein or polypeptide.

The term "activity" as used herein shall be understood as a measure for the ability of a substance, such as transcription product or a translation product, to produce a biological effect or a measure for a level of biologically active molecules. The term "activity" also refers to biological activity and/or pharmacological activity which refers to binding, antagonization, repression, blocking, neutralization or sequestration of a kinase or kinase subunit and which refers to activation, agonization, up-regulation of a kinase or kinase subunit.

The terms "level" and/or "activity" as used herein further refer to gene expression levels or gene activity. Gene expression can be defined as the utilization of the information contained in a gene by transcription and translation leading to the production of a gene product.

"Dysregulation" shall mean an up-regulation or down-regulation of gene expression and/or an increase or decrease in the stability of the gene products. A gene product comprises either RNA or protein and is the result of expression of a gene. The amount of a gene product can be used to measure how active a gene is and how stable its gene products are.

The term "gene" as used in the present specification and in the claims comprises both coding regions (exons) as well as non-coding regions (e.g. non-coding regulatory elements such as promoters or enhancers, introns, leader and trailer sequences).

The term "ORF" is an acronym for "open reading frame" and refers to a nucleic acid sequence that does not possess a stop codon in at least one reading frame and therefore can potentially be translated into a sequence of amino acids.

"Regulatory elements" shall comprise inducible and non-inducible promoters, enhancers, operators, and other elements that drive and regulate gene expression.

The term "fragment" as used herein is meant to comprise e.g. an alternatively spliced, or truncated, or otherwise cleaved transcription product or translation product.

The term "derivative" as used herein refers to a mutant, or an RNA-edited, or a chemically modified, or otherwise altered transcription product, or to a mutant, or chemically modified, or otherwise altered translation product. For the purpose of clarity, a derivative transcript, for instance, refers to a transcript having alterations in the nucleic acid sequence such as single or multiple nucleotide deletions, insertions, or exchanges. A derivative translation product, for instance, may be generated by processes such as altered phosphorylation, or glycosylation, or acetylation, or lipidation, or by altered signal peptide cleavage or other types of maturation cleavage. These processes may occur post-translationally.

The term "modulator" as used in the present invention and in the claims refers to a molecule capable of changing or altering the level and/or the activity of a gene, or a transcription product of a gene, or a translation product of a gene. A "modulator" refers to a molecule which has the capacity to either enhance or inhibit, thus to "modulate" a functional property of a protein, to "modulate" binding, antagonization, repression, blocking, neutralization or sequestration, activation, agonization and up-regulation. "Modulation" will be also used to refer to the capacity to affect the biological activity of a cell. Preferably, a "modulator" is capable of changing or altering the biological activity of a transcription product or a translation product of a gene. Said modulation, for instance, may be an increase or a decrease in the biological activity and/or pharmacological activity, a change in binding characteristics, or any other change or alteration in the biological, functional, or immunological properties of said translation product of a gene.

The terms "agent", "reagent", or "compound" refer to any substance, chemical, composition, or extract that have a positive or negative biological effect on a cell, tissue, body fluid, or within the context of any biological system, or any assay system examined. They can be agonists, antagonists, partial agonists or inverse agonists of a target. Such agents, reagents, or compounds may be nucleic acids, natural or synthetic peptides or protein complexes, or fusion proteins. They may also be antibodies, organic or anorganic molecules or compositions, small molecules, drugs and any combinations of any of said agents above. They may be used for testing, for diagnostic or for therapeutic purposes.

The terms "oligonucleotide primer" or "primer" refer to short nucleic acid sequences which can anneal to a given target polynucleotide by hybridization of the complementary base pairs and can be extended by a polymerase. They may be chosen to be specific to a particular sequence or they may be randomly selected, e.g. they will prime all possible sequences in a mix. The length of primers used herein may vary from 10 nucleotides to 80 nucleotides. "Probes" are short nucleic acid sequences of the nucleic acid sequences described and disclosed herein or sequences complementary therewith. They may comprise full length sequences, or fragments, derivatives, isoforms, or variants of a given sequence. The identification of hybridization complexes between a "probe" and an assayed sample allows the detection of the presence of other similar sequences within that sample.

As used herein, "homolog or homology" is a term used in the art to describe the relatedness of a nucleotide or peptide sequence to another nucleotide or peptide sequence, which is determined by the degree of identity and/or similarity between said sequences compared.

In the art, the terms "identity" and "similarity" mean the degree of polypeptide or polynucleotide sequence relatedness which are determined by matching a query sequence and other sequences of preferably the same type (nucleic acid or protein sequence) with each other. Preferred computer program methods to calculate and determine "identity" and "similarity" include, but are not limited to GCG BLAST (Basic Local Alignment Search Tool) (Altschul et al., *J. Mol. Biol.* 1990, 215: 403-410; Altschul et al., *Nucleic Acids Res.* 1997, 25: 3389-3402; Devereux et al., *Nucleic Acids Res.* 1984, 12: 387), BLASTN 2.0 (Gish W., http://blast.wustl.edu, 1996-2002), FASTA (Pearson and Lipman, *Proc. Natl. Acad. Sci. USA* 1988, 85: 2444-2448), and GCG GelMerge which determines and aligns a pair of contigs with the longest overlap (Wilbur and Lipman, *SIAM J. Appl. Math.* 1984, 44: 557-567; Needleman and Wunsch, *J. Mol. Biol.* 1970, 48: 443-453).

The term "variant" as used herein refers to any polypeptide or protein, in reference to polypeptides and proteins disclosed in the present invention, in which one or more amino acids are added and/or substituted and/or deleted and/or inserted at the N-terminus, and/or the C-terminus, and/or within the native amino acid sequences of the native polypeptides or proteins of the present invention, but retains its essential properties. Furthermore the term "variant" as used herein refers to any mRNA, in reference to gene transcripts disclosed in the present invention, in which one or more nucleotides are added and/or substituted and/or deleted.

Furthermore, the term "variant" shall include any shorter or longer version of a polypeptide or protein. "Variants" shall also comprise a sequence that has at least about 80% sequence identity, more preferably at least about 85% sequence identity, and most preferably at least about 90% sequence identity over a length of at least 200 amino acids of PRKX protein, SEQ ID NO: 1. "Variants" include, for example, a variant of PRKX protein having SEQ ID NO: 1 is PRKY (UniProt primary accession number O43930) having SEQ ID NO: 2. Variants also include proteins with conservative amino acid substitutions in highly conservative regions. It may be advantageous not to use in the present invention fragments, derivatives or variants of the PKA protein (proteinase K) which fragments are identical to PKA subunits.

Furthermore, the term "variant" shall include any shorter or longer version of a gene transcript. "Variants" shall also comprise a sequence that has at least about 80% sequence identity, more preferably at least about 85% sequence identity, and most preferably at least about 90% sequence identity over a length of at least 600 nucleotides of PRKX gene transcript, SEQ ID NO: 3. Sequence variations shall be included wherein a codon is replaced with another codon due to alternative base sequences, but the amino acid sequence translated by the DNA sequence remains unchanged. This known in the art phenomenon is called redundancy of the set of codons which translate specific amino acids.

"Proteins and polypeptides" of the present invention include variants, fragments and chemical derivatives of the protein comprising the amino acid sequence of PRKX protein, SEQ ID NO: 1. Included shall be such exchange of amino acids which would have no effect on functionality, such as arginine for lysine, valine for leucine, asparagine for glutamine. Proteins and polypeptides can be included which can be isolated from nature or be produced by recombinant and/or synthetic means. Native proteins or polypeptides refer to naturally-occurring truncated or secreted forms, naturally occurring variant forms (e.g. splice-variants) and naturally occurring allelic variants. The term "isolated" as used herein is considered to refer to molecules or substances which have been changed and/or that are removed from their natural environment, i.e. isolated from a cell or from a living organism in which they normally occur, and that are separated or essentially purified from the coexisting components with which they are found to be associated in nature. This notion further means that the sequences encoding such molecules can be linked by the hand of man to polynucleotides, to which they are not linked in their natural state and such molecules can be produced by recombinant and/or synthetic means, it is also said that they are "non-native". Even if for said purposes those sequences may be introduced into living or non-living organisms by methods known to those skilled in the art, and even if those sequences are still present in said organisms, they are still considered to be isolated. In the present invention, the terms "risk", "susceptibility", and "predisposition" are tantamount and are used with respect to the probability of developing a neurodegenerative disease, preferably Alzheimer's disease.

The term "AD" shall mean Alzheimer's disease. "AD-type neuropathology", "AD pathology" as used herein refers to neuropathological, neurophysiological, histopathological and clinical hallmarks, signs and symptoms as described in the instant invention and as commonly known from state-of-the-art literature (see: Iqbal, Swaab, Winblad and Wisniewski, *Alzheimer's Disease and Related Disorders (Etiology, Pathogenesis and Therapeutics)*, Wiley & Sons, New York, Weinheim, Toronto, 1999; Scinto and Daffner, *Early Diagnosis of Alzheimer's Disease*, Humana Press, Totowa, N.J., 2000; Mayeux and Christen, *Epidemiology of Alzheimer's Disease: From Gene to Prevention*, Springer Press, Berlin, Heidelberg, N.Y., 1999; Younkin, Tanzi and Christen, *Presenilins and Alzheimer's Disease*, Springer Press, Berlin, Heidelberg, N.Y., 1998).

The term "Braak stage" or "Braak staging" refers to the classification of brains according to the criteria proposed by Braak and Braak (Braak and Braak, *Acta Neuropathology* 1991, 82: 239-259). Braak staging of AD rates the extent and distribution of neurofibrillary pathology in determined regions of the forebrain and divides the neuropathologic progression of AD into six stages (stage 0 to 6). It is a well established and universally accepted procedure in post-mortem neuropathological staging of AD. It has convincingly been shown that there is a significant correlation between an AD patient's clinical condition with respect to mental status and cognitive function/impairment and the corresponding Braak stage obtained after autopsy (Bancher et al., *Neuroscience Letters* 1993, 162:179-182; Gold et al., Acta Neuropathol 2000, 99: 579-582). Likewise, a correlation between neurofibrillary changes and neuronal cellular pathology has been found (Rössler et al., Acta Neuropathol 2002, 103:363-369), and both have been reported to predict cognitive function (Giannakopoulos et al., Neurology 2003, 60:1495-1500; Bennett et al., Arch Neurol 2004, 61:378-384). Moreover, a pathogenic cascade has been proposed that involves the deposition of beta-amyloid peptide and finally cumulates in the formation of neurofibrillary tangles, the latter thus witnessing the precedence of earlier AD-specific events at the molecular/cellular level (Metsaars et al., Neurobiol Aging 2003, 24:563-572).

In the instant invention, Braak stages are therefore used as a surrogate marker of disease progression independent of the clinical presentation/condition of the individual donor, i.e. independent of the presence or absence of reported mental illness, cognitive deficits, decline in other neuropsychiatric parameters, or the overt clinical diagnosis of AD. I.e. it is presumed that the neurofibrillary changes on which the Braak staging reflect the underlying molecular and cellular pathomechanisms in general and hence define a (pre-)morbid condition of the brain, meaning that e.g. a donor staged Braak 1 represents by definition an earlier stage of molecular/cellular pathogenesis than a donor staged 2 (or higher), and that therefore a donor of Braak stage 1 can e.g. be regarded as a control individual when compared to donors of any higher Braak stage. In this regard, the differentiation between control individual and affected individual may not necessarily be the same as the clinical diagnosis based differentiation between healthy control donor and AD patient, but it rather refers to a presumed difference in the (pre-) morbid status as deduced from and mirrored by a surrogate marker, the Braak stage.

In the instant invention Braak stage 0 may represent persons which are not considered to suffer from Alzheimer's disease signs and symptoms, and Braak stages 1 to 4 may represent either healthy, control individuals or AD patients depending on whether said individuals were suffering already from clinical signs and symptoms of AD. The higher the Braak stage the more likely is the possibility to display signs and symptoms of AD or the risk to develop signs and symptoms of AD. For a neuropathological assessment, i.e. an estimation of the probability that pathological changes of AD are the underlying cause of dementia, a recommendation is given by Braak H. (www.alzforum.org).

The values obtained from controls are the reference values representing a known health status and the values obtained from patients are the reference values representing a known disease status.

Neurodegenerative diseases or disorders according to the present invention comprise Alzheimer's disease, Parkinson's disease, Huntington's disease, amyotrophic lateral sclerosis, Pick's disease, fronto-temporal dementia, progressive nuclear palsy, corticobasal degeneration, cerebro-vascular dementia, multiple system atrophy, argyrophilic grain dementia and other tauopathies, and mild-cognitive impairment. Further conditions involving neurodegenerative processes are, for instance, ischemic stroke, age-related macular degeneration, narcolepsy, motor neuron diseases, prion diseases, traumatic nerve injury and repair, and multiple sclerosis.

The present invention discloses the identification, the differential expression, the differential regulation, a dysregulation of a gene of the serine/threonine-protein kinase family PRKX, and of the protein products of said gene PRKX, in specific samples, in specific brain regions of AD patients, in specific brain regions of individuals grouped into different Braak stages, in comparison with each other and/or in comparison to age-matched control individuals. The present invention discloses that the gene expression for PRKX is varied, is dysregulated in brains of AD patients as compared to the respective brain regions of control individuals, in that PRKX mRNA levels are increased, are up-regulated in the temporal cortex and in the frontal cortex of AD patients. Further, the present invention discloses that the PRKX expression differs in specific brain regions of individuals grouped into different Braak stages with an increase in expression level starting already at early Braak stages (Braak 1-3) and with a progressive increase with the course of late Braak stages (Braak 4-6) predominantly in the inferior temporal cortex.

The differences observed at the PRKX gene transcriptional level, when compared between AD patients and control individuals but also between the different Braak stages, are further supported by substantial differences that can be found at the PRKX protein level. In contrast to the control individuals, in brain specimens from AD patients the PRKX protein is contained at high levels in reactive astrocytes, accumulates and co-localizes with CD68 protein within plaque-associated activated microglia, and co-deposits with cortical beta-amyloid plaques. This dysregulation of the PRKX gene expression and the changes in levels and localization of the corresponding gene products which parallels the development of AD-type pathology clearly reflects a link between PRKX and AD and is indicative for the progressive pathological events in the course of the disease. Further evidence for this link is provided by the finding that the Drosophila PRKX ortholog pka-C3 accelerates the degenerative phenotype in a Drosophila AD model and that this effect is accompanied by an increase in the pathological phosphorylation of a mutant form of the tau protein. More specifically, the pka-C3 kinase increases the phosphorylation of Ser214, an amino acid position in tau that has been demonstrated to be abnormally phosphorylated in AD. Therefore PRKX may be causally involved in the cascade of molecular pathological events leading to AD and therefore may represent a promising target for the identification and development of small molecule based therapeutics for AD and other neurodegenerative diseases. To date, no experiments have been described that demonstrate a relationship between the dysregulation of the PRKX gene expression and the changes in levels and localization of the corresponding gene products and the pathology of neurodegenerative diseases, in particular AD. Likewise, no mutations in the PRKX gene have been described to be associated with said diseases. Linking the PRKX gene to such diseases offers new ways, inter alia, for the diagnosis and treatment of said diseases. Additionally, linking PRKX to pathological events occurring already early in the course of AD provides the possibility of a treatment which will prevent the initiation of AD pathology, a treatment which will be applied before non-repairable damages of the brain occur. Consequently, the present invention has utility for diagnostic evaluation, for diagnostic monitoring of persons undergoing a treatment, for prognosis as well as for the identification of a predisposition to a neurodegenerative disease, in particular AD.

The present invention discloses a dysregulation of a gene coding for PRKX and of its gene products in specific brain regions of AD patients. Neurons within the inferior temporal lobe, the entorhinal cortex, the hippocampus, and the amygdala are subject to degenerative processes in AD (Terry et al., *Annals of Neurology* 1981, 10:184-192). These brain regions are mostly involved in the processing of learning and memory functions and display a selective vulnerability to neuronal loss and degeneration in AD. In contrast, neurons within the frontal cortex, the occipital cortex, and the cerebellum remain largely intact and preserved from neurodegenerative processes. Brain tissues from the frontal cortex (F) and the inferior temporal cortex (T) of AD patients and of age-matched controls were used for the herein disclosed examples. Consequently, the PRKX gene and its corresponding transcription and/or translation products play a causative role, have an influence on the selective neuronal degeneration and/or neuroprotection.

In one aspect, the invention features a method of diagnosing or prognosticating a neurodegenerative disease in a subject, or determining whether a subject has a predisposition of developing said disease, is at increased risk of developing said disease, or of monitoring the effect of a treatment administered to a subject having a neurodegenerative disease. The method comprises: determining a level, an expression or an activity, or both said level, expression and said activity of (i) a transcription product of a gene coding for PRKX proteins, and/or of (ii) a translation product of a gene coding for PRKX proteins, and/or of (iii) a fragment, or derivative, or variant of said transcription or translation product in a sample obtained from said subject and comparing said level, expression and/or said activity of said transcription product and/or said translation product and/or said fragment, derivative or variant thereof to a reference value representing a known disease status (patient) and/or to a reference value representing a known health status (control), and/or to a reference value representing a known Braak stage and analysing whether said level and/or said activity is varied, is altered compared to a reference value representing a known health status, and/or is similar or equal to a reference value representing a known disease status and/or is similar compared to a reference value representing a known Braak stage which is an indication that said subject has a neurodegenerative disease, or that said subject is at increased risk of developing signs and symptoms of said disease, thereby diagnosing or prognosticating said neurodegenerative disease in said subject, or determining whether said subject is at increased risk of developing said neurodegenerative disease. The wording "in a subject" refers to results of the methods disclosed as far as they relate to a disease afflicting a subject, that is to say, said disease being "in" a subject.

In a further aspect, the invention features a method of monitoring the progression of a neurodegenerative disease in a subject. A level, expression or an activity, or both said level, expression and said activity, of (i) a transcription product of a gene coding for PRKX proteins, and/or of (ii) a translation product of a gene coding for PRKX proteins, and/or of (iii) a fragment, or derivative, or variant of said transcription or translation product in a sample obtained from said subject is determined. Said level, expression and/or said activity are compared to a reference value representing a known disease or health status or a known Braak stage. Thereby, the progression of said neurodegenerative disease in said subject is monitored.

In still a further aspect, the invention features a method of evaluating a treatment or monitoring the effect of a treatment for a neurodegenerative disease, comprising determining a level, expression or an activity, or both said level, expression and said activity of (i) a transcription product of a gene coding for PRKX proteins, and/or of (ii) a translation product of a gene coding for PRKX proteins, and/or of (iii) a fragment, or derivative, or variant of said transcription or translation product in a sample obtained from a subject being treated for said disease. Said level, expression or said activity, or both said level, expression and said activity are compared to a reference value representing a known disease or health status or a known Braak stage, thereby evaluating the treatment for said neurodegenerative disease.

In a preferred embodiment, the level, expression or the activity, or both said level and said activity of (i) a transcription product of a gene coding for PRKX proteins, and/or of (ii) a translation product of a gene coding for PRKX proteins, and/or of (iii) a fragment, or derivative, or variant of said transcription or translation product in a series of samples taken from said subject over a period of time is compared, in order to monitor the progression of said disease. In further preferred embodiments, said subject receives a treatment prior to one or more of said sample gatherings. In yet another preferred embodiment, said level and/or activity is determined before and after said treatment of said subject.

It is preferred that said level, the expression and/or said activity of said transcription product and/or said translation product of PRKX and of its fragments, derivatives, or variants, is increased, is up-regulated in samples obtained from AD patients as compared to samples obtained from persons not suffering from AD, control persons. For example, the expression and/or activity of the transcription product and/or the translation product of PRKX and of its fragments, derivatives, or variants is measured from samples of patients and compared with the expression and/or activity of the transcription product and/or the translation product of PRKX and of its fragments, derivatives, or variants in a sample of a healthy control subject (reference sample).

In a preferred embodiment of the herein claimed methods, kits, recombinant animals, molecules, assays, and uses of the instant invention, said PRKX gene and proteins, is represented by the PRKX gene coding for the protein of SEQ ID NO: 1 (Genbank accession number P51817). Furthermore it may be preferred to use the PRKY gene coding for the protein of SEQ ID NO: 2 (UniProt primary accession number O43930). The amino acid sequences of said proteins are deduced from the mRNA sequences of SEQ ID NO: 3 or SEQ ID NO: 4 which correspond to the cDNA sequences of Genbank accession numbers BC041073 or Ensembl transcript ID number ENST00000311978. In the instant preferred embodiment of the invention PRKX also refers to the nucleic acid sequences SEQ ID NO: 5 or SEQ ID NO: 6 representing the coding sequence (cds) of human PRKX or PRKY, respectively. In the instant invention said sequences are "isolated" as the term is employed herein.

In a further preferred embodiment of the herein claimed methods, kits, recombinant animals, molecules, assays, and uses of the instant invention, said neurodegenerative disease or disorder is Alzheimer's disease, and said subjects suffer from signs and symptoms of Alzheimer's disease.

It is preferred that the sample to be analyzed and determined is selected from the group comprising brain tissue or other tissues, or body cells. The sample can also comprise cerebrospinal fluid or other body fluids including saliva, urine, stool, blood, serum plasma, or mucus. Preferably, the methods of diagnosis, prognosis, monitoring the progression or evaluating a treatment for a neurodegenerative disease, according to the instant invention, can be practiced ex corpore, and such methods preferably relate to samples, for instance, body fluids or cells, removed, collected, or isolated from a subject or patient or a control person.

In further preferred embodiments, said reference value is that of a level, of expression, or of an activity, or both said level and said activity of (i) a transcription product of the gene coding for PRKX proteins, and/or of (ii) a translation product of the gene coding for PRKX proteins, and/or of (iii) a fragment, or derivative, or variant of said transcription or translation product in a sample obtained from a subject not suffering from said neurodegenerative disease (control sample, control, healthy control person) or in a sample obtained from a subject suffering from a neurodegenerative disease, in particular Alzheimer's disease (patient sample, patient, AD sample) or from a person with a defined Braak stage which may suffer or may not suffer from signs and symptoms of AD.

In preferred embodiments, an alteration in the level and/or activity and/or expression of a transcription product of the gene coding for PRKX proteins and/or of a translation product of the gene coding for PRKX proteins and/or of a fragment, or derivative, or variant thereof in a sample cell, or tissue, or body fluid taken from said subject relative to a reference value representing a known health status (control sample) indicates a diagnosis, or prognosis, or increased risk of becoming diseased with a neurodegenerative disease, particularly AD.

In further preferred embodiments, an equal or similar level and/or activity and/or expression of a transcription product of the gene coding for PRKX proteins and/or of a translation product of the gene coding for PRKX proteins and/or of a fragment, or derivative, or variant thereof in a sample cell, or tissue, or body fluid obtained from a subject relative to a reference value representing a known disease status of a neurodegenerative disease, in particular Alzheimer's disease (AD patient sample), indicates a diagnosis, or prognosis, or increased risk of becoming diseased with said neurodegenerative disease.

In another further preferred embodiment, an equal or similar level, expression and/or activity of a transcription product of the gene coding for a PRKX proteins and/or of a translation product of the gene coding for a PRKX proteins and/or of a fragment, or derivative, or variant thereof in a sample cell, or tissue, or body fluid obtained from a subject relative to a reference value representing a known Braak stage which Braak stage reflects a high risk of developing signs and symptoms of AD, indicates a diagnosis, or prognosis, or an increased risk of becoming diseased with AD.

It is preferred however that said varied, altered level, altered expression and/or said altered activity of said transcription product and/or said translation product of PRKX and of its fragments, derivatives, or variants, is an increase, an up-regulation.

In preferred embodiments, measurement of the level of transcription products and/or of expression of the gene coding for PRKX proteins is performed in a sample obtained from a subject using a quantitative PCR-analysis with primer combinations to amplify said gene specific sequences from cDNA obtained by reverse transcription of RNA extracted from a sample of a subject. Primer combinations (SEQ ID NO: 7, SEQ ID NO: 8) are given in Example (iv) of the instant invention, but also other primers generated from the sequences as disclosed in the instant invention can be used. A Northern blot or a ribonuclease protection assay (RPA) with probes specific for said gene can also be applied. It might further be preferred to measure transcription products by means of chip-based microarray technologies. These techniques are known to those of ordinary skill in the art (see Sambrook and Russell, *Molecular Cloning: A Laboratory Manual*, Cold Spring Harbor Laboratory Press, Cold Spring Harbor, N.Y., 2001; Schena M., *Microarray Biochip Technol-*

*ogy*, Eaton Publishing, Natick, Mass., 2000). An example of an immunoassay is the detection and measurement of enzyme activity as disclosed and described in the patent application WO02/14543.

The invention also relates to the construction and the use of primers and probes which are unique to the nucleic acid sequences, or fragments, or variants thereof, as disclosed in the present invention. The oligonucleotide primers and/or probes can be labeled specifically with fluorescent, bioluminescent, magnetic, or radioactive substances. The invention further relates to the detection and the production of said nucleic acid sequences, or fragments and variants thereof, using said specific oligonucleotide primers in appropriate combinations. PCR-analysis, a method well known to those skilled in the art, can be performed with said primer combinations to amplify said gene specific nucleic acid sequences from a sample containing nucleic acids. Such sample may be derived either from healthy or diseased subjects or subjects with defined Braak stages. Whether an amplification results in a specific nucleic acid product or not, and whether a fragment of different length can be obtained or not, may be indicative for a neurodegenerative disease, in particular Alzheimer's disease. Thus, the invention provides nucleic acid sequences, oligonucleotide primers, and probes of at least 10 bases in length up to the entire coding and gene sequences, useful for the detection of gene mutations and single nucleotide polymorphisms in a given sample comprising nucleic acid sequences to be examined, which may be associated with neurodegenerative diseases, in particular Alzheimer's disease. This feature has utility for developing rapid DNA-based diagnostic tests, preferably also in the format of a kit. Primers for PRKX are exemplarily described in Example 1 (vi).

Furthermore, a level and/or an activity and/or expression of a translation product of the gene coding for PRKX proteins and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, *Immunodiagnostics: A Practical Approach*, Oxford University Press, Oxford; England, 1999). All these detection techniques may also be employed in the format of microarrays, protein-arrays, antibody microarrays, tissue microarrays, electronic biochip or protein-chip based technologies (see Schena M., *Microarray Biochip Technology*, Eaton Publishing, Natick, Mass., 2000).

In another aspect, the invention features a kit for diagnosing or prognosticating neurodegenerative diseases, in particular AD, in a subject, or determining the propensity or predisposition of a subject to develop a neurodegenerative disease, in particular AD, or of monitoring the effect of a treatment administered to a subject having a neurodegenerative disease, particularly AD, said kit comprising:
(a) at least one reagent which is selected from the group consisting of (i) reagents that detect a transcription product of the gene coding for PRKX proteins (ii) reagents that detect a translation product of the gene coding for PRKX proteins, and/or reagents that detect a fragment or derivative or variant of said transcription or translation product;
(b) instructions for diagnosing, or prognosticating a neurodegenerative disease, in particular AD, or determining the propensity or predisposition of a subject to develop such a disease or of monitoring the effect of a treatment by
  determining a level, or an activity, or both said level and said activity, and/or expression of said transcription product and/or said translation product and/or of fragments, derivatives or variants of the foregoing, in a sample obtained from said subject; and
  comparing said level and/or said activity and/or expression of said transcription product and/or said translation product and/or fragments, derivatives or variants thereof to a reference value representing a known disease status (patient) and/or to a reference value representing a known health status (control) and/or to a reference value representing a known Braak stage; and
  analysing whether said level and/or said activity and/or expression is varied compared to a reference value representing a known health status, and/or is similar or equal to a reference value representing a known disease status or a reference value representing a known Braak stage; and
  diagnosing or prognosticating a neurodegenerative disease, in particular AD, or determining the propensity or predisposition of said subject to develop such a disease, wherein a varied or altered level, expression or activity, or both said level and said activity, of said transcription product and/or said translation product and/or said fragments, derivatives or variants thereof compared to a reference value representing a known health status (control) and/or wherein a level, or activity, or both said level and said activity, of said transcription product and/or said translation product and/or said fragments, derivatives or variants thereof is similar or equal to a reference value representing a known disease status (patient sample), preferably a disease status of AD (AD patient), and/or to a reference value representing a known Braak stage, indicates a diagnosis or prognosis of a neurodegenerative disease, in particular AD, or an increased propensity or predisposition of developing such a disease, a high risk of developing signs and symptoms of AD. The kit, according to the present invention, may be particularly useful for the identification of individuals that are at risk of developing a neurodegenerative disease, in particular AD.

Reagents that selectively detect a transcription product and/or a translation product of the gene coding for PRKX proteins can be sequences of various length, fragments of sequences, antibodies, aptamers, siRNA, microRNA, and ribozymes. Such reagents may be used also to detect fragments, derivatives or variants thereof.

In a further aspect the invention features the use of a kit in a method of diagnosing or prognosticating a neurodegenerative disease, in particular Alzheimer's disease, in a subject, and in a method of determining the propensity or predisposition of a subject to develop such a disease, and in a method of monitoring the effect of a treatment administered to a subject having a neurodegenerative disease, particularly AD.

Consequently, the kit, according to the present invention, may serve as a means for targeting identified individuals for early preventive measures or therapeutic intervention prior to disease onset, before irreversible damage in the course of the disease has been inflicted. Furthermore, in preferred embodiments, the kit featured in the invention is useful for monitoring a progression of a neurodegenerative disease, in particular AD in a subject, as well as monitoring success or failure of therapeutic treatment for such a disease of said subject.

In another aspect, the invention features a method of treating or preventing a neurodegenerative disease, in particular AD, in a subject comprising the administration to said subject in need of such a treatment in a therapeutically or prophylactically effective amount and formulation an agent, agents, modulators antagonist, agonists or antibodies which directly or indirectly affect a level, or an activity, or both said level and said activity, of (i) the gene coding for PRKX proteins, and/or (ii) a transcription product of the gene coding for PRKX proteins, and/or (iii) a translation product of the gene coding for PRKX proteins, and/or (iv) a fragment, or derivative, or variant of (i) to (iii). Said agent may comprise a small molecule, or it may also comprise a peptide, an oligopeptide, or a polypeptide. Said peptide, oligopeptide, or polypeptide may comprise an amino acid sequence of a translation product of the gene coding for PRKX proteins, or a fragment, or derivative, or a variant thereof. An agent for treating or preventing a neurodegenerative disease, in particular AD, according to the instant invention, may also consist of a nucleotide, an oligonucleotide, or a polynucleotide. Said oligonucleotide or polynucleotide may comprise a nucleotide sequence of the gene coding for PRKX proteins, either in sense orientation or in antisense orientation.

In preferred embodiments, the method comprises the application of per se known methods of gene therapy and/or antisense nucleic acid technology to administer said agent or agents. In general, gene therapy includes several approaches: molecular replacement of a mutated gene, addition of a new gene resulting in the synthesis of a therapeutic protein, and modulation of endogenous cellular gene expression by recombinant expression methods or by drugs. Gene-transfer techniques are described in detail (see e.g. Behr, *Acc Chem Res* 1993, 26: 274-278 and Mulligan, *Science* 1993, 260: 926-931) and include direct gene-transfer techniques such as mechanical microinjection of DNA into a cell as well as indirect techniques employing biological vectors (like recombinant viruses, especially retroviruses) or model liposomes, or techniques based on transfection with DNA co-precipitation with polycations, cell membrane pertubation by chemical (solvents, detergents, polymers, enzymes) or physical means (mechanic, osmotic, thermic, electric shocks). The postnatal gene transfer into the central nervous system has been described in detail (see e.g. Wolff, *Curr Opin Neurobiol* 1993, 3: 743-748).

In particular, the invention features a method of treating or preventing a neurodegenerative disease by means of antisense nucleic acid therapy, i.e. the down-regulation of an inappropriately expressed or defective gene by the introduction of antisense nucleic acids or derivatives thereof into certain critical cells (see e.g. Gillespie, DN&P 1992, 5: 389-395; Agrawal and Akhtar, *Trends Biotechnol* 1995, 13: 197-199; Crooke, *Biotechnology* 1992, 10: 882-6). Apart from hybridization strategies, the application of ribozymes, i.e. RNA molecules that act as enzymes, destroying RNA that carries the message of disease has also been described (see e.g. Barinaga, *Science* 1993, 262: 1512-1514). In preferred embodiments, the subject to be treated is a human, and therapeutic antisense nucleic acids or derivatives thereof are directed against transcription products, of the gene coding for PRKX proteins. It is preferred that cells of the central nervous system, preferably the brain, of a subject are treated in such a way. Cell penetration can be performed by known strategies such as coupling of antisense nucleic acids and derivatives thereof to carrier particles, or the above described techniques.

Strategies for administering targeted therapeutic oligodeoxynucleotides are known to those of skill in the art (see e.g. Wickstrom, *Trends Biotechnol* 1992, 10: 281-287). In some cases, delivery can be performed by mere topical application. Further approaches are directed to intracellular expression of antisense RNA. In this strategy, cells are transformed ex vivo with a recombinant gene that directs the synthesis of an RNA that is complementary to a region of target nucleic acid. Therapeutical use of intracellularly expressed antisense RNA is procedurally similar to gene therapy. A recently developed method of regulating the intracellular expression of genes by the use of double-stranded RNA, known variously as RNA interference (RNAi), can be another effective approach for nucleic acid therapy (Hannon, *Nature* 2002, 418: 244-251).

In further preferred embodiments, the method comprises grafting donor cells into the central nervous system, preferably the brain, of said subject, or donor cells preferably treated so as to minimize or reduce graft rejection, wherein said donor cells are genetically modified by insertion of at least one transgene encoding said agent or agents. Said transgene might be carried by a viral vector, in particular a retroviral vector. The transgene can be inserted into the donor cells by a nonviral physical transfection of DNA encoding a transgene, in particular by microinjection. Insertion of the transgene can also be performed by electroporation, chemically mediated transfection, in particular calcium phosphate transfection or liposomal mediated transfection (see Mc Celland and Pardee, *Expression Genetics: Accelerated and High-Throughput Methods*, Eaton Publishing, Natick, Mass., 1999).

In preferred embodiments, said agent for treating and preventing a neurodegenerative disease, in particular AD, is a therapeutic protein which can be administered to said subject, preferably a human, by a process comprising introducing subject cells into said subject, said subject cells having been treated in vitro to insert a DNA segment encoding said therapeutic protein, said subject cells expressing in vivo in said subject a therapeutically effective amount of said therapeutic protein. Said DNA segment can be inserted into said cells in vitro by a viral vector, in particular a retroviral vector.

Methods of treatment or prevention, according to the present invention, comprise the application of therapeutic cloning, transplantation, and stem cell therapy using embryonic stem cells or embryonic germ cells and neuronal adult stem cells, combined with any of the previously described cell- and gene therapeutic methods. Stem cells may be totipotent or pluripotent. They may also be organ-specific. Strategies for repairing diseased and/or damaged brain cells or tissue comprise (i) taking donor cells from an adult tissue. Nuclei of those cells are transplanted into unfertilized egg cells from which the genetic material has been removed. Embryonic stem cells are isolated from the blastocyst stage of the cells which underwent somatic cell nuclear transfer. Use of differentiation factors then leads to a directed development of the stem cells to specialized cell types, preferably neuronal cells (Lanza et al., *Nature Medicine* 1999, 9: 975-977), or (ii) purifying adult stem cells, isolated from the central nervous system, or from bone marrow (mesenchymal stem cells), for in vitro expansion and subsequent grafting and transplantation, or (iii) directly inducing endogenous neural stem cells to proliferate, migrate, and differentiate into functional neurons (Peterson D A, *Curr. Opin. Pharmacol.* 2002, 2: 34-42) Adult neural stem cells are of great potential for repairing damaged or diseased brain tissues, as the germinal centers of the adult brain are free of neuronal damage or dysfunction (Colman A, *Drug Discovery World* 2001, 7: 66-71).

In preferred embodiments, the subject for treatment or prevention, according to the present invention, can be a human, or a non-human experimental animal, e.g. a mouse or a rat, a domestic animal, or a non-human primate. The experimental animal can be an animal model for a neurodegenerative disorder, e.g. a transgenic mouse and/or a knock-out mouse with an AD-type neuropathology.

In a further aspect, the invention features an agent, antagonist or agonist or a modulator of an activity, or a level, or both said activity and said level, and/or of expression of at least one substance which is selected from the group consisting of (i) a gene coding for PRKX proteins, and/or (ii) a transcription product of the gene coding for PRKX proteins, and/or (iii) a translation product of the gene coding for PRKX proteins, and/or (iv) a fragment, or derivative, or variant of (i) to (iii), and said agent, antagonist or agonist, or said modulator has a potential activity in the treatment of neurodegenerative diseases, in particular AD.

In another aspect, the invention provides for the use of an agent, an antibody, a antagonist or agonist, or a modulator of an activity, or a level, or both said activity and said level, and/or of expression of at least one substance which is selected from the group consisting of (i) the gene coding for PRKX proteins, and/or (ii) a transcription product of the gene coding for PRKX proteins, and/or (iii) a translation product of the gene coding for PRKX proteins, and/or (iv) a fragment, or derivative, or variant of (i) to (iii) in the manufacture of a medicament for treating or preventing a neurodegenerative disease, in particular AD. Said antibody may be specifically immunoreactive with an immunogen which is a translation product of a gene coding for PRKX proteins having SEQ ID NO: 1 or a fragment, or a derivative, or variant thereof, in particular the variant having the SEQ ID NO: 2.

In an additional aspect, the invention features a pharmaceutical composition comprising said agent, antibody, antagonist or agonist, or modulator and preferably a pharmaceutical carrier. Said carrier refers to a diluent, adjuvant, excipient, or vehicle with which the modulator is administered.

Another aspect of the invention concerns a medicament comprising an antagonist of a level and/or of activity and/or of expression of at least one substance which is selected from the group consisting of
(i) a gene coding for PRKX proteins, and/or
(ii) a transcription product of the gene coding for PRKX proteins, and/or
(iii) a translation product of the gene coding for PRKX proteins, and/or
(iv) fragments, or derivatives, or variants of (i) to (iii)
which antagonist is selected from the group consisting of an antisense nucleic acid, an antibody or antibody fragments, siRNA, ribozyme, aptamer and combinations thereof.

As antibody or antibody fragment also the following substances are understood: a Fab fragment, monovalent fragment consisting of the VL, VH, CL and CH I domains; a F (ab) 2 or F (ab') 2 fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment; an isolated complementarity determining region (CDR); and single chain Fv (scFv) antibodies, scfv, f(ab) fragments.

In one aspect, the present invention also provides a kit comprising one or more containers filled with a therapeutically or prophylactically effective amount of said pharmaceutical composition.

In a further aspect, the invention features a recombinant, genetically modified non-human animal comprising a non-native PRKX gene sequence coding for PRKX proteins having in particular SEQ ID NO: 1, or a fragment, or a derivative, or variant thereof (e.g. the variant having the SEQ ID NO: 2) under the control of a transcriptional element which is not the native PRKX gene transcriptional control element. The generation of said recombinant, non-human animal comprises (i) providing a gene targeting construct containing said gene sequence and a selectable marker sequence, and (ii) introducing said targeting construct into a stem cell of a non-human animal, and (iii) introducing said non-human animal stem cell into a non-human embryo, and (iv) transplanting said embryo into a pseudopregnant non-human animal, and (v) allowing said embryo to develop to term, and (vi) identifying a genetically altered non-human animal whose genome comprises a modification of said gene sequence in both alleles, and (vii) breeding the genetically altered non-human animal of step (vi) to obtain a genetically altered non-human animal whose genome comprises a modification of said gene sequence, wherein the expression of said gene, a mis-expression, under-expression, non-expression or over-expression, and wherein the disruption or alteration of said gene sequence results in said non-human animal exhibiting a predisposition to developing signs and symptoms of a neurodegenerative disease, in particular AD. Strategies and techniques for the generation and construction of such an animal are known to those of ordinary skill in the art (see e.g. Capecchi, *Science* 1989, 244: 1288-1292 and Hogan et al., *Manipulating the Mouse Embryo: A Laboratory Manual*, Cold Spring Harbor Laboratory Press, Cold Spring Harbor, N.Y., 1994 and Jackson and Abbott, *Mouse Genetics and Transgenics: A Practical Approach*, Oxford University Press, Oxford, England, 1999).

It is preferred to make use of such a genetically modified, recombinant non-human animal as an animal model, as test animal or as a control animal for investigating neurodegenerative diseases, in particular Alzheimer's disease. Such an animal may be useful for screening, testing and validating compounds, agents and modulators in the development of diagnostics and therapeutics to treat neurodegenerative diseases, in particular Alzheimer's disease. The use of such a genetically modified animal in a screening method is disclosed in the instant invention.

In a further aspect the invention makes use of a cell, in which a gene sequence coding for PRKX proteins having in particular SEQ ID NO: 1, or a fragment, or derivative, or variant thereof (e.g. the variant having the SEQ ID NO: 2) is mis-expressed, under-expressed, non-expressed or over-expressed, or disrupted or in another way, altered for screening, testing and validating compounds, agents and modulators in the development of diagnostics and therapeutics to treat neurodegenerative diseases, in particular Alzheimer's disease. The use of such a cell in a screening method is disclosed in the instant invention.

In another aspect, the invention features method of screening for an agent, a modulator, a antagonist or agonist for use in the treatment or prevention of neurodegenerative diseases, in particular AD, or related diseases and disorders, which agents, modulators or antagonists or agonists have an ability to alter expression and/or level and/or activity of one or more substances selected from the group consisting of (i) the gene coding for PRKX proteins having in particular SEQ ID NO: 1, and/or (ii) a transcription product of the gene coding for PRKX proteins having in particular SEQ ID NO: 1, and/or (iii) a translation product of the gene coding for PRKX proteins having in particular SEQ ID NO: 1, and/or (iv) a fragment, or derivative, or variant of (i) to (iii), e.g. the variant having the SEQ ID NO: 2. This screening method comprises (a) contacting a cell with a test compound, and (b) measuring the activity and/or the level, or both the activity and the level, and/or the expression of one or more substances recited in (i) to (iv), and (c) measuring the activity and/or the level, or both the activity and the level and/or the expression of said substances in a control cell not contacted with said test compound, and (d) comparing the levels and/or activities and/or the expression of the substance in the cells of step (b) and (c), wherein an alteration in the activity and/or level and/or expression of said substances in the contacted cells indicates that the test compound is an agent, modulator, antagonist or agonist for use in the treatment or prevention of neurodegenerative diseases and disorders. Said cells may be cells as disclosed in the instant invention.

In one further aspect, the invention features a method of screening for an agent, a modulator, a antagonist or agonist for use in the treatment or prevention of neurodegenerative diseases, in particular AD, or related diseases and disorders which agents, modulators or antagonists or agonists have an ability to alter expression and/or level and/or activity of one or more substances selected from the group consisting of (i) the gene coding for PRKX proteins having in particular SEQ, ID NO: 1, and/or (ii) a transcription product of the gene coding for PRKX proteins having in particular SEQ ID NO: 1, and/or (iii) a translation product of the gene coding for PRKX proteins having in particular SEQ ID NO: 1, and/or (iv) a fragment, or derivative, or variant of (i) to (iii), e.g. the variant having the SEQ ID NO: 2. comprising (a) administering a test compound to a non-human test animal which is predisposed to developing or has already developed signs and symptoms of a neurodegenerative disease or related diseases or disorders, said animal may be an animal model as disclosed in the instant invention, and (b) measuring the activity and/or level and/or expression of one or more substances recited in (i) to (iv), and (c) measuring the activity and/or level and/or expression of said substances in a non-human control animal which is equally predisposed to developing or has already developed said signs and symptoms of a neurodegenerative disease or related diseases or disorders, and to which non-human animal no such test compound has been administered, and (d) comparing the activity and/or level and/or expression of the substances in the animals of step (b) and (c), wherein an alteration in the activity and/or level and/or expression of substances in the non-human test animal indicates that the test compound is an agent, modulator, antagonist or agonist for use in the treatment or prevention of neurodegenerative diseases and disorders.

In another embodiment, the present invention provides a method for producing a medicament comprising the steps of (i) identifying an agent, modulator, antagonists or agonists of neurodegenerative diseases by a method of the aforementioned screening assays and (ii) admixing said agent, modulator, antagonist or agonist with a pharmaceutical carrier. However, said agent, modulator, antagonist or agonist may also be identifiable by other types of screening methods and assays.

In another aspect, the present invention provides for an assay for testing a compound or compounds, preferably for screening a plurality of compounds in high-throughput format, to determine the degree of inhibition of binding or the enhancement of binding between a ligand and PRKX proteins having in particular SEQ ID NO:1, or a fragment, or derivative, or variant thereof (e.g. the variant having the SEQ ID NO: 2) and/or to determine the degree of binding of said compounds to PRKX proteins having in particular SEQ ID NO:1, or a fragment, or derivative, or variant thereof (e.g. the variant having the SEQ ID NO: 2). For determination of inhibition of binding between a ligand and PRKX proteins, or a fragment, or derivative, or variant thereof, said screening assay comprises the steps of (i) adding a liquid suspension of said PRKX proteins, or a fragment, or derivative, or variant thereof, to a plurality of containers, and (ii) adding a compound or a plurality of compounds to be screened for said inhibition to said plurality of containers, and (iii) adding a detectable, preferably a fluorescently labelled ligand to said containers, and (iv) incubating said PRKX proteins, or said fragment, or derivative or variant thereof, and said compound or plurality of compounds, and said detectable, preferably fluorescently labelled ligand, and (v) measuring preferably the amounts of the fluorescence associated with said PRKX proteins, or with said fragment, or derivative, or variant thereof, and (vi) determining the degree of inhibition by one or more of said compounds of binding of said ligand to said PRKX proteins, or said fragment, or derivative, or variant thereof. It might be preferred to reconstitute said PRKX translation products, or fragment, or derivative, or variant thereof into artificial liposomes to generate the corresponding proteoliposomes to determine the inhibition of binding between a ligand and said PRKX translation products. Methods of reconstitution of PRKX translation products from detergent into liposomes have been detailed (Schwarz et al., *Biochemistry* 1999, 38: 9456-9464; Krivosheev and Usanov, *Biochemistry-Moscow* 1997, 62: 1064-1073). Instead of utilizing a fluorescently labelled ligand, it might in some aspects be preferred to use any other detectable label known to the person skilled in the art, e.g. radioactive labels, and detect it accordingly. Said method may be useful for the identification of novel compounds as well as for evaluating compounds which have been improved or otherwise optimized in their ability to inhibit the binding of a ligand to a gene product of the gene coding for PRKX proteins, or a fragment, or derivative, or variant thereof. One example of a fluorescent binding assay, in this case based on the use of carrier particles, is disclosed and described in patent application WO00/52451. A further example is the competitive assay method as described in patent WO02/01226. Preferred signal detection methods for screening assays of the instant invention are described in the following patent applications: WO96/13744, WO98/16814, WO98/23942, WO99/17086, WO99/34195, WO00/66985, WO01/59436, WO01/59416.

In one further embodiment, the present invention provides a method for producing a medicament comprising the steps of (i) identifying a compound as an inhibitor of binding between a ligand and a gene product of the gene coding for PRKX proteins by the aforementioned inhibitory binding assay and (ii) admixing the compound with a pharmaceutical carrier. However, said compound may also be identifiable by other types of screening assays.

Furthermore the present invention provides an assay for testing a compound or compounds, preferably for screening a plurality of compounds in high-throughput format to determine the degree of binding of said compounds to PRKX proteins having in particular SEQ ID NO: 1, or to a fragment, or derivative, or variant thereof (e.g. the variant having the SEQ ID NO: 2), said screening assay comprises (i) adding a liquid suspension of said PRKX proteins, or a fragment, or derivative, or variant thereof, to a plurality of containers, and (ii) adding a detectable, preferably a fluorescently labelled compound or a plurality of detectable, preferably fluorescently labelled compounds to be screened for said binding to said plurality of containers, and (iii) incubating said PRKX proteins, or said fragment, or derivative, or variant thereof, and said detectable, preferably fluorescently labelled compound or detectable, preferably fluorescently labelled compounds, and (iv) measuring the amounts of preferably the fluorescence associated with said PRKX proteins, or with said fragment, or derivative, or variant thereof, and (v) determining the degree of binding by one or more of said compounds to said PRKX proteins, or said fragment, or derivative, or variant thereof. In this type of assay it might be preferred to use a fluorescent label. However, any other type of detectable label might also be employed. Also in this type of assay it might be preferred to reconstitute a PRKX translation product or a fragment, or derivative, or variant thereof into artificial liposomes as described in the present invention. Said assay methods may be useful for the identification of novel compounds as well as for evaluating compounds which have been improved or otherwise optimized in their ability to bind to PRKX proteins, or a fragment, or derivative, or variant thereof.

In one further embodiment, the present invention provides a method for producing a medicament comprising the steps of (i) identifying a compound as a binder to a gene product of the gene coding for PRKX proteins by the aforementioned binding assays and (ii) admixing the compound with a pharmaceutical carrier. However, said compound may also be identifiable by other types of screening assays.

In another embodiment, the present invention provides for a medicament obtainable by any of the methods according to the herein claimed screening assays. In one further embodiment, the instant invention provides for a medicament obtained by any of the methods according to the herein claimed screening assays.

Another aspect of the present invention features protein molecules and the use of said protein molecules having SEQ ID NO: 1, said protein molecules being translation products of the gene coding for PRKX, or fragments, or derivatives, or variants thereof (e.g. the variant having the SEQ ID NO: 2), as diagnostic targets for detecting a neurodegenerative disease, in particular Alzheimer's disease.

The present invention further features protein molecules and the use of said protein molecules having SEQ ID NO: 1, said protein molecules being translation products of the gene coding for PRKX, or fragments, or derivatives, or variants thereof (e.g. the variant having the SEQ ID NO: 2), as screening targets for agents, modulators, antagonists, agonists, reagents or compounds preventing, or treating, or ameliorating a neurodegenerative disease, in particular Alzheimer's disease.

The present invention features antibodies which are specifically immunoreactive with an immunogen, wherein said immunogen is a translation product of the PRKX gene coding for PRKX proteins having in particular SEQ ID NO: 1, or fragments, or derivatives, or variants thereof (e.g. the variant having the SEQ ID NO: 2). The immunogen may comprise immunogenic or antigenic epitopes or portions of a translation product of said gene, wherein said immunogenic or antigenic portion of a translation product is a polypeptide, and wherein said polypeptide elicits an antibody response in an animal, and wherein said polypeptide is immunospecifically bound by said antibody. Methods for generating antibodies are well known in the art (see Harlow et al., *Antibodies, A Laboratory Manual*, Cold Spring Harbor Laboratory Press, Cold Spring Harbor, N.Y., 1988). The term "antibody", as employed in the present invention, encompasses all forms of antibodies known in the art, such as polyclonal, monoclonal, chimeric, recombinatorial, anti-idiotypic, humanized, or single chain antibodies, as well as fragments thereof (see Dubel and Breitling, *Recombinant Antibodies*, Wiley-Liss, New York, N.Y., 1999). Antibodies of the present invention are useful, for instance, in a variety of diagnostic and therapeutic methods, based on state-in-the-art techniques (see Harlow and Lane, *Using Antibodies: A Laboratory Manual*, Cold Spring Harbor Laboratory Press, Cold Spring Harbor, N.Y., 1999 and Edwards R., *Immunodiagnostics: A Practical Approach*, Oxford University Press, Oxford, England, 1999) such as enzyme-immuno assays (e.g. enzyme-linked immunosorbent assay, ELISA), radioimmuno assays, chemoluminescence-immuno assays, Western-blot, immunoprecipitation and antibody microarrays. These methods involve the detection of translation products of the PRKX gene, or fragments, or derivatives, or variants thereof.

In a preferred embodiment of the present invention, said antibodies can be used for detecting the pathological state of a cell in a sample obtained from a subject, comprising immunocytochemical staining of said cell with said antibody, wherein an altered degree of staining, or an altered staining pattern in said cell compared to a cell representing a known health status indicates a pathological state of said cell. Preferably, the pathological state relates to a neurodegenerative disease, in particular to AD. Immunocytochemical staining of a cell can be carried out by a number of different experimental methods well known in the art. It might be preferred, however, to apply an automated method for the detection of antibody binding, wherein the determination of the degree of staining of a cell, or the determination of the cellular or subcellular staining pattern of a cell, or the topological distribution of an antigen on the cell surface or among organelles and other subcellular structures within the cell, are carried out according to the method described in U.S. Pat. No. 6,150,173.

Other features and advantages of the invention will be apparent from the following description of figures and examples which are illustrative only and not intended to limit the remainder of the disclosure in any way.

FIGURES

FIG. 1 shows the identification of differences in the levels of PRKX gene derived mRNA in human brain tissue samples from individuals corresponding to different Braak stages as measured and compared by GeneChip analyses. It indicates that the levels of the respective mRNA species correlate quantitatively with AD progression and thus are indicative for AD as measured by the neuropathological staging of brain tissue samples according to Braak and Braak (Braak staging). cRNA probes of frontal cortex as well as of inferior temporal cortex each of 5 different donors with Braak stage 0 (C01, C012, C026, C027, and C032), 7 different donors with Braak stage 1 (C014, C028, C029, C030, C036, C038, and C039), 5 different donors with Braak stage 2 (C008, C031, C033, C034, and DE03), 4 different donors with Braak stage 3 (C025, DE07, DE11, and C057), and 4 different donors with Braak stage 4 (P012, P046, P047, and P068) have been applied to an analysis of an Affymetrix Human Genome U133 Plus 2.0 Array respectively. Differences reflecting an up-regulation of the PRKX gene progressively with Braak stages predominantly in inferior temporal tissue are shown.

FIG. 2 lists the data for the verification of differences in the levels of PRKX gene derived mRNA in human brain tissue samples from individuals corresponding to different Braak stages indicative for AD as measured by quantitative RT-PCR analysis. Quantitative RT-PCR using the Roche Lightcycler rapid thermal cycling technique was performed applying cDNA of the frontal cortex (Frontal) and the inferior temporal cortex (Temporal) of the same donors as used for GeneChip analysis. The data were normalized to values of cyclophilin B a standard gene that showed no significant differences in its gene expression levels. The comparison between samples of the lowest Braak stage 0 with samples representing high Braak stage 4 clearly demonstrates a substantial difference in gene expression level of PRKX.

FIG. 3 shows the analysis of absolute levels of PRKX gene derived mRNA in human brain tissue samples from individuals corresponding to different Braak stages indicative for AD as measured by quantitative RT-PCR and using statistical method of the median at 98%-confidence level (Sachs L (1988) Statistische Methoden Planung und Auswertung. Heidelberg N.Y., p. 60). The data were calculated by defining control groups including subjects with Braak stages 0 to 2, which are compared with the data calculated for the defined groups with advanced AD pathology including Braak stages 3 to 4. A substantial difference reflecting an up-regulation is shown in frontal as well as in inferior temporal cortices corroborating results from the GeneChip analysis. Most prominent difference is obvious comparing inferior temporal cortex (T) of Braak stage 0-2 with Braak stage 3-4. Said difference reflects an up-regulation of PRKX in the temporal cortex and in the frontal cortex of individuals with advanced AD pathology relative to the inferior temporal cortex and the frontal cortex of control persons, and an up-regulation of PRKX in the inferior temporal cortex of individuals with advanced AD pathology compared to their frontal cortices.

FIG. 4A discloses SEQ ID NO: 1, the amino acid sequence of the human PRKX protein (Genbank accession number P51817). The full length human PRKX protein comprises 358 amino acids.

FIG. 4B discloses SEQ ID NO: 2, the amino acid sequence of the human PRKY protein (UniProt primary accession number 043930). The full length human PRKY protein comprises 277 amino acids.

FIG. 5A shows SEQ ID NO: 3, the nucleotide sequence of the human PRKX cDNA (Genbank accession number BC041073) encoding the PRKX protein, comprising 2350 nucleotides.

FIG. 5B shows SEQ ID NO: 4, the nucleotide sequence of the human PRKY cDNA (Ensembl transcript ID number ENST00000311978) encoding the PRKY protein, comprising 895 nucleotides.

FIG. 6A depicts SEQ ID NO: 5, the coding sequence (cds) of the human PRKX gene, comprising 1077 nucleotides, harbouring nucleotides 185 to 1261 of SEQ ID NO. 3.

FIG. 6B depicts SEQ ID NO: 6, the coding sequence (cds) of the human PRKY gene, comprising 834 nucleotides, harbouring nucleotides 18 to 852 of SEQ ID NO. 4.

FIG. 7 depicts the sequence alignment of the primers used for PRKX transcription level profiling (primer A, SEQ ID NO: 7 and primer B, SEQ ID NO: 8) by quantitative RT-PCR with the corresponding clippings of SEQ ID NO: 3, PRKX cDNA.

FIG. 8 schematically charts the alignment of the PRKX cDNA sequence SEQ ID NO: 3, the PRKX coding sequence SEQ ID NO: 5 and both primer sequences used for PRKX transcription level profiling (SEQ ID NO: 7, SEQ ID NO: 8). Sequence positions are indicated on the right side.

Figure 9:
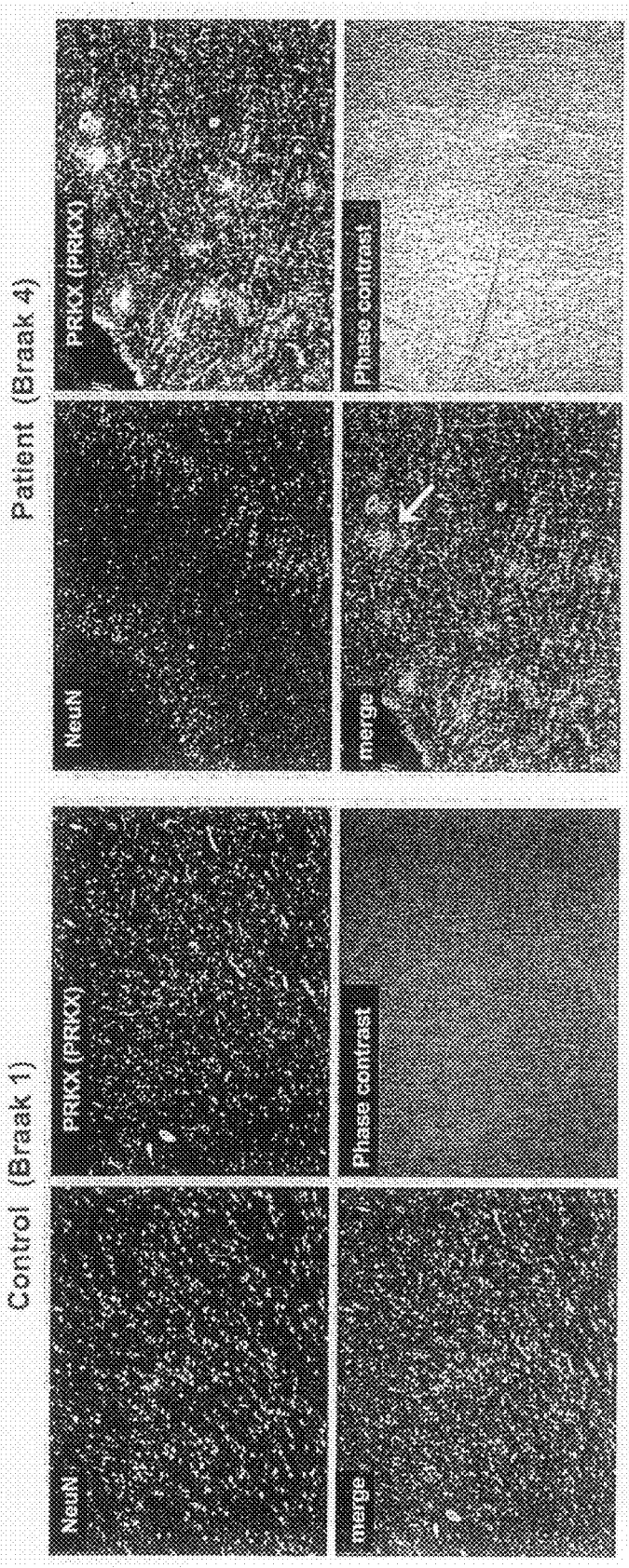
FIG. 9 exemplifies the co-deposition of PRKX protein with cortical beta-amyloid plaques in human brain specimens from AD patients (Braak stage 4). In contrast no such deposition of PRKX protein is observed in brain specimens from age-matched controls (Braak stage 0) which have not been diagnosed to suffer from AD signs and symptoms.

FIG. 9 exemplifies the co-deposition of PRKX protein with cortical beta-amyloid plaques observed in human brain specimens from AD patients. In contrast no such deposition of PRKX protein is observed in brain specimens from age-matched non-AD control individuals. The typical example demonstrates the general finding that PRKX protein is co-deposited with amyloid plaques (e.g. arrow) in patients, which is absent from controls. Depicted are double-immunofluorescence micrographs (original magnification ×4) of acetone-fixed cryostat sections of fresh-frozen post-mortem human brain temporal cortex specimens from an AD patient and an age-matched non-AD control, at Braak stages 4 and 1, respectively. Specific PRKX immunoreactivity is revealed by the affinity-purified polyclonal rabbit anti-PRKX antiserum (Abgent) followed by AlexaFluor-488 conjugated goat anti-rabbit IgG secondary antiserum (Molecular Probes/Invitrogen), visualized as either grayscale images (right upper quadrant of each panel) or green signals in the merged image (left lower quadrant of each panel). The neuron-specific somatic marker protein NeuN is detected by the mouse monoclonal anti-NeuN antibody (Chemicon) followed by Cy3-conjugated goat anti-mouse IgG secondary antiserum (Jackson/Dianova), visualized as either grayscale images (left upper quadrant of each panel) or red signals in the merged image (left lower quadrant of each panel). Nuclei are stained blue by DAPI (Sigma). The right lower quadrants show the corresponding phase contrast images.

Figure 10:
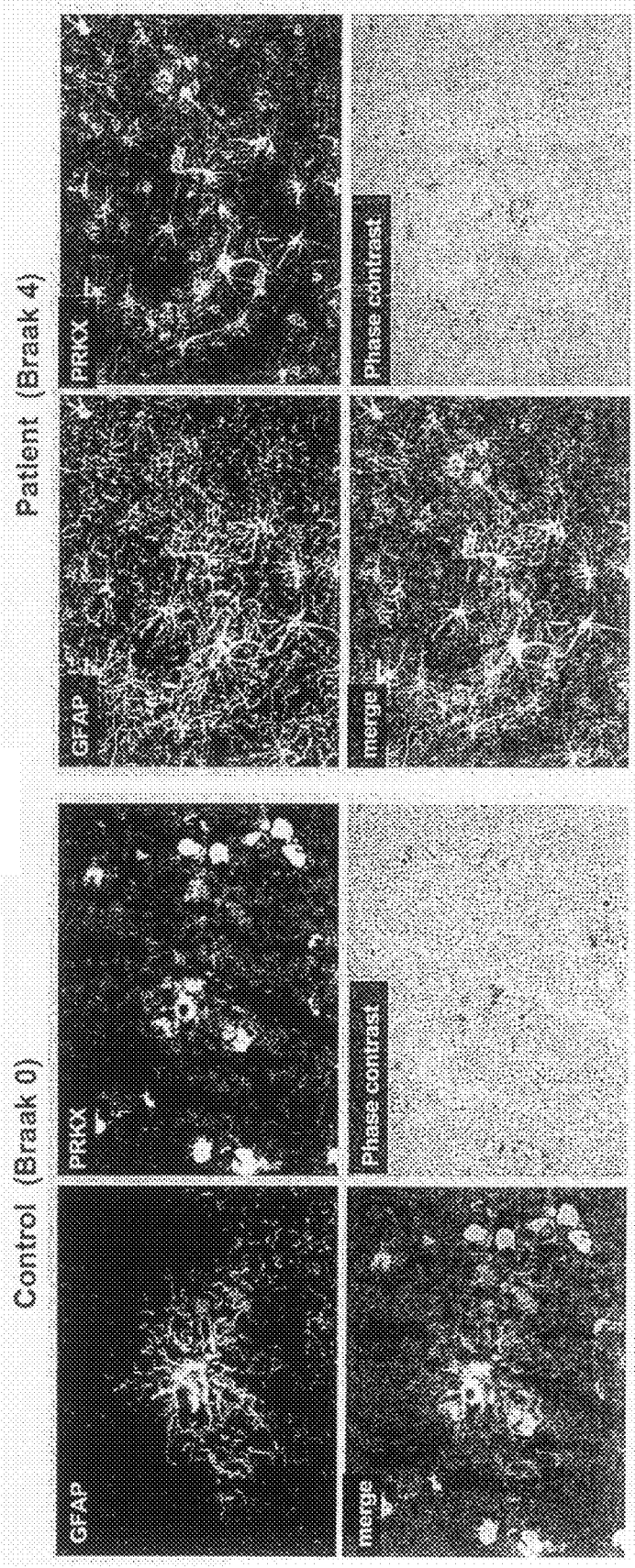
FIG. 10 exemplifies that reactive astrocytes in the cortex of AD patients (Braak stage 4) contain the PRKX protein at high levels. In contrast only low levels of PRKX protein can be found in astrocytes in the cortex of age-matched controls (Braak stage 0) which have not been diagnosed to suffer from AD signs and symptoms.

FIG. 10 exemplifies that reactive astrocytes in the cortex of AD patients contain the PRKX protein at high levels. In contrast only low levels of PRKX protein can be found in astrocytes in the cortex of age-matched control individuals not affected by AD. Depicted are double-immunofluorescence micrographs of acetone-fixed cryostat sections of fresh-frozen post-mortem human brain temporal cortex specimens from an AD patient (original magnification ×20) and an age-matched non-AD control (original magnification ×40), at Braak stages 4 and 0, respectively. Specific PRKX immunoreactivity is revealed by the affinity-purified polyclonal rabbit anti-PRKX antiserum (Abgent) followed by AlexaFluor-488 conjugated goat anti-rabbit IgG secondary antiserum (Molecular Probes/Invitrogen), visualized as either grayscale images (right upper quadrant of each panel) or green signals in the merged image (left lower quadrant of each panel). The astrocyte-specific marker protein GFAP is detected by the mouse monoclonal anti-GFAP antibody (Abcam) followed by Cy3-conjugated goat anti-mouse IgG secondary antiserum (Jackson/Dianova), visualized as either grayscale images (left upper quadrant of each panel) or red signals in the merged image (left lower quadrant of each panel). Nuclei are stained blue by DAPI (Sigma). The right lower quadrants show the corresponding phase contrast images. The left panel shows one typical astrocyte in the control specimen (power ×40). The right panel shows the characteristic appearance of many reactive astrocytes in the AD specimen (power ×20).

Figure 11:
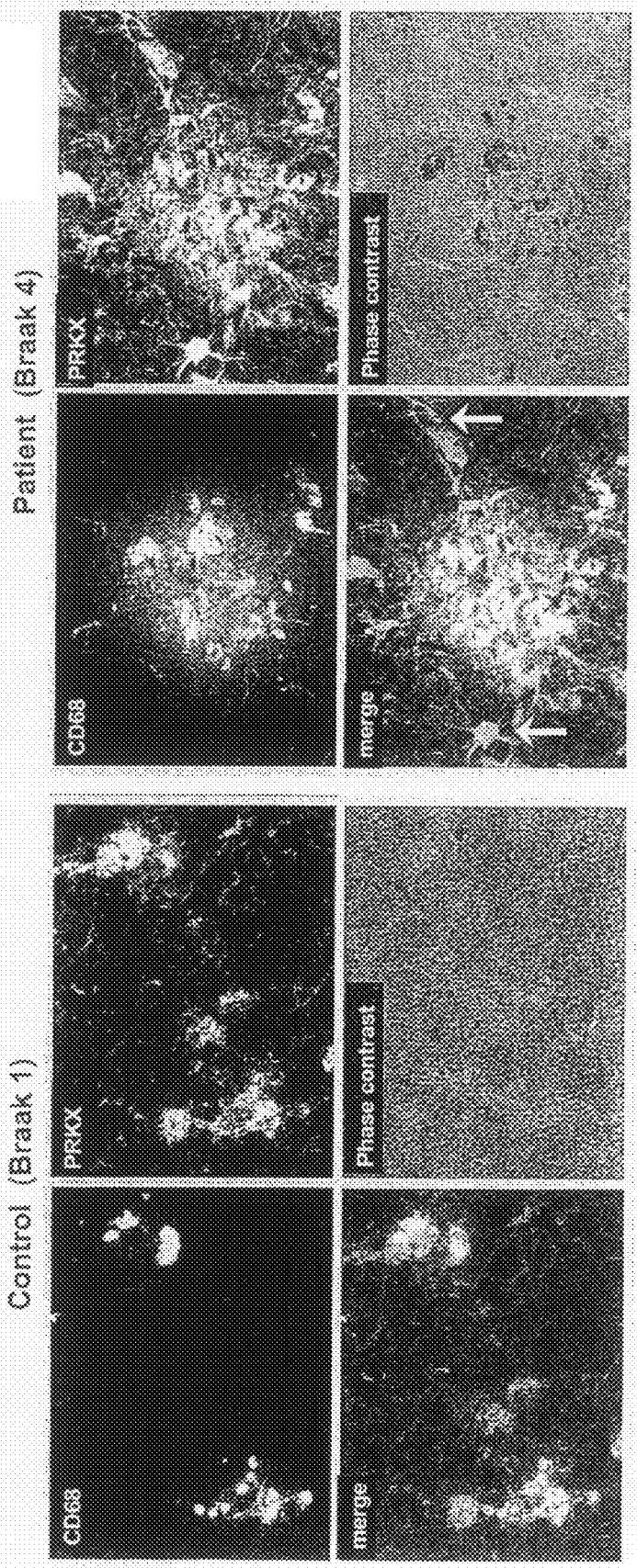
FIG. 11 exemplifies that PRKX protein is massively accumulated and co-localized with CD68 protein within plaque-associated activated microglia in brain tissue samples from AD patients (Braak 4). In contrast, such accumulation of the PRKX protein is not observed in brain tissue samples from age-matched controls (Braak 1) which have not been diagnosed to suffer from AD signs and symptoms.

FIG. 11 exemplifies that PRKX protein is massively accumulated and co-localized with CD68 protein within plaque-associated activated microglia in brain tissue samples from AD patients. In contrast, such accumulation of the PRKX protein is not observed in brain tissue samples from age-matched control individuals not affected by AD. Depicted are double-immunofluorescence micrographs of acetone-fixed cryostat sections of fresh-frozen post-mortem human brain temporal cortex specimens from an AD patient (original magnification ×40) and an age-matched non-AD control (original magnification ×100), at Braak stages 4 and 1, respectively. Specific PRKX immunoreactivity is revealed by the affinity-purified polyclonal rabbit anti-PRKX antiserum (Abgent) followed by AlexaFluor-488 conjugated goat anti-rabbit IgG secondary antiserum (Molecular Probes/Invitrogen), visualized as either grayscale images (right upper quadrant of each panel) or green signals in the merged image (left lower quadrant of each panel). The microglia-specific marker protein CD68 is detected by the mouse polyclonal anti-CD68 antibody (Dako) followed by Cy3-conjugated goat anti-mouse IgG secondary antiserum (Jackson/Dianova), visualized as either grayscale images (left upper quadrant of each panel) or red signals in the merged image (left lower quadrant of each panel). Nuclei are stained blue by DAPI (Sigma). The right lower quadrants show the corresponding phase contrast images. The left panel shows two typical microglial cells in the control specimen (power ×100). The right panel shows the characteristic appearance of many activated microglia populating an amyloid plaque in the AD specimen (power ×40). The micrographs characteristically illustrate that CD68 protein is massively expressed by plaque-associated activated microglia, and that PRKX protein is simultaneously accumulated and co-localized, resulting in strong yellow merge signals, a finding which in contrast is absent from control samples. In addition, the example clearly demonstrates that PRKX protein expression by reactive astrocytes is typically enhanced in AD (arrows) as compared to controls.

FIG. 12 shows the detection of mRNA expression of pka-C3, the Drosophila ortholog of the human PRKX gene, in transgenic flies. Depicted is the detection of pka-C3 expression in two different pka-C3 transgenic fly lines expressed under the control of gmr-GAL4 by RT-PCR using pka-C3 specific primers. The efficiency of the reaction is calculated according to the cycle number and efficiency of the RT-PCR reaction of the pka-C3 specific primer pair (E=1.86). Based on this calculation pka-C3 in line pka-C3 [03065] is 2.7 times higher expressed than in control flies whereas pka-C3 in line [02687] is down-regulated compared to control flies. Measurements were done in triplicates for each genotype. Genotypes used were: w; P(EPgy2)Pka-C3EY02687/gmr-GAL4; w; P{EPgy2}Pka-C3EY03065/gmr-GAL4 and w; gmr-GAL4/+.

Figure 13:
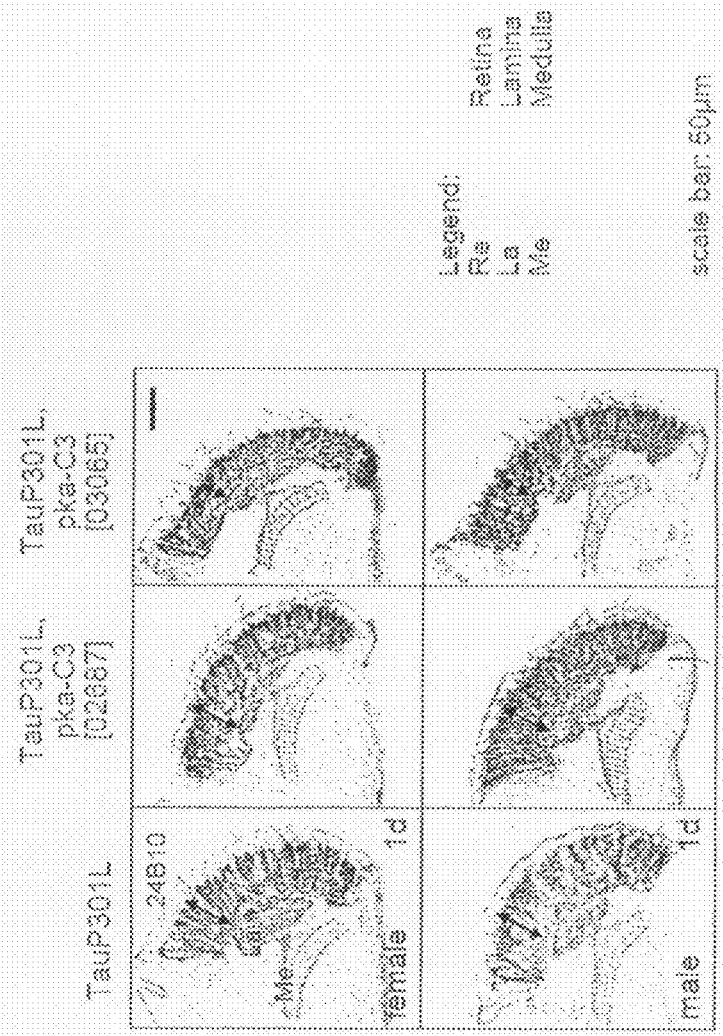
FIG. 13 shows that overexpression of the Drosophila PRKX ortholog pka-C3 accelerates a TauP301L induced photoreceptor cell degeneration in transgenic flies as judged by the diameter of the fly retina.

FIG. 13 shows that overexpression of the Drosophila PRKX ortholog pka-C3 accelerates a TauP301L induced photoreceptor cell degeneration in an AD transgenic fly model. Expression of pka-C3 (03065) accelerates TauP301L induced photoreceptor cell degeneration of flies expressing hTauP301L under the control of gmr-GAL4 as judged by the diameter of the retina (black arrows). Co-expression of pka-C3 (02687, partial loss-of-function) has no effect on the TauP301L induced phenotype. Genotypes used were: w; P(EPgy2)Pka-C3EY03065/gmr-GAL4, UAS-TauP301L— w; P{EPgy2}Pka-C3EY02687/gmr-GAL, UAS-TauP301L—w; gmr-GAL4, UAS-TauP301L/+.

Figure 14:
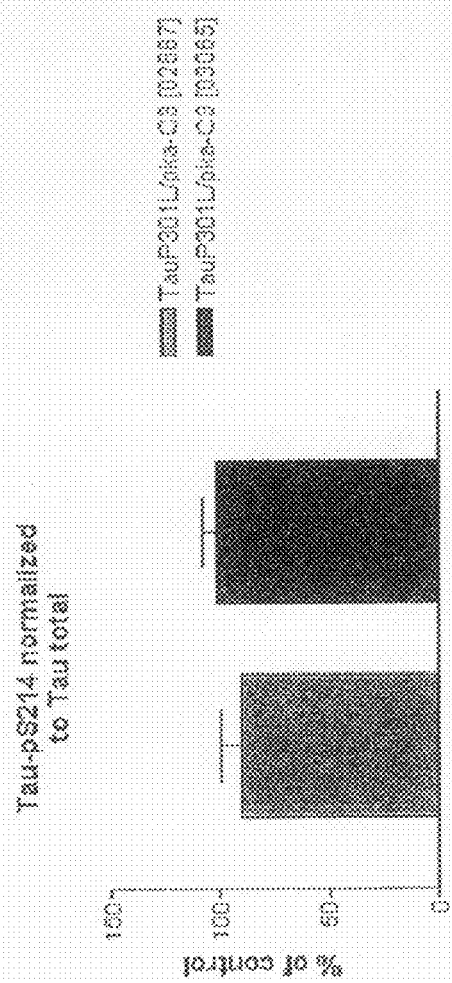
FIG. 14 shows that the Drosophila PRKX ortholog pka-C3 is involved in the phosphorylation of Ser214 of TauP301L in flies co-expressing TauP301L and pka-C3. Partial loss-of-function of pka-C3 (02687) reduces phosphorylation of TauP301L at Ser214 in comparison to flies co-expressing a wt pka-C3 (03065) transgene.

FIG. 14 shows that the Drosophila PRKX ortholog pka-C3 is involved in the phosphorylation of Ser214 of TauP301L in flies co-expressing TauP301L and pka-C3. Partial loss-of-function of pka-C3 (02687) reduces phosphorylation of TauP301L at Ser214 in comparison to flies co-expressing a wt pka-C3 (03065) transgene. Depicted is the quantification of phosphorylated Ser214 of TauP301L that reveals an increase in phosphorylation of TauP310L in flies co-expressing TauP301L and pka-C3 (03065) in comparison to control flies whereas a partial loss-of-function of pka-C3 (02687) may slightly decrease phosphorylation of Tau at Ser214 (data do not reach significance). Statistical analysis was done using GraphPad Prism 3.02. Genotypes used were: w; P{EPgy2}Pka-C3EY03065/gmr-GAL4, UAS-TauP301L— w; P{EPgy2}Pka-C3EY02687/gmr-GAL, UAS-TauP301L—w; gmr-GAL4, UAS-TauP301L/+.

FIG. 15 shows Western blot-analysis of inducible PRKX protein production in H4-neuroglioma cells stably co-expressing the Swedish Mutant APP. PRKX was myc-tagged at the C-terminus and introduced into tissue culture cells. Expression of PRKX is under the control of the tet-operator-sequence fused to the CMV-promoter. Upon addition of 1 µg/ml tetracycline into the medium the expression of PRKX is switched on. Cells were harvested, lysed and subjected to Western Blot analysis using an antibody directed against the myc-epitope at a 1:3000 dilution. The arrow points to a strong band running at approx. 43 kDa. In the absence of tetracycline only a faint band running at the same molecular weight is visible possibly pointing to background expression due to leakiness of the inducible promoter.

FIG. 16 shows the immunofluorescence analysis of inducible PRKX protein production in H4-neuroglioma cells stably co-expressing the Swedish Mutant APP and the tet-repressor. PRKX was myc-tagged at the C-terminus and introduced into tissue culture cells. Expression of PRKX is under the control of the tet-operator-sequence fused to the CMV-promoter. Upon addition of 1 µg/ml tetracycline into the medium the expression of PRKX in the cells that were seeded onto a glass cover slip is switched on. After 24 hours of incubation, cells where fixed with methanol for immunofluorescence analysis and expression of PRKX was detected using an antibody directed against the myc-epitope at a 1:3000 dilution followed by incubation with a fluorescently labelled antibody directed against the anti-myc antibody (1:1000). Cells were then mounted onto a microscope slide and analysed under a fluorescence microscope. Expression of PRKX is visible in the cytoplasm of the cells in the upper left and middle pictures due to the strong green fluorescence. In the lower panel control cells have been analysed in parallel and no green fluorescence can be detected. The blue colour in the upper and lower left and right pictures are indicative of the nucleus of the cells and have been visualized by means of DAPI (1:1000).

FIG. 17 depicts the targeting strategy for transgenic mice expressing human PRKX in neurons. The targeting vector is composed of the transgene and Rosa26 homology sequences in order to integrate the transgene into the Rosa26 gene locus. The short homology arm (SA) consists of approximately 1.1 kb, the long homology arm (LA) consists of about 4.3 kb. The 3 exons of the Rosa26 gene are indicated with roman numbers. The transgene is composed of the open reading frame of the human PRKX (ORF PRKX) which is located in the murine Thy1.2 expression cassette containing regulatory sequences of the brain-specific Thy1.2 gene. 5'prime of the transgene a Neomycin resistance gene (Neo) and a splice acceptor are located allowing expression of the Neo selection marker driven by the Rosa promoter from the endogenous Rosa26 gene. 3'prime of the Neo marker a poly A signal (pA) will stop transcription.

EXAMPLE 1

Identification and Verification of Alzheimer's Disease Related Differentially Expressed Genes in Human Brain Tissue Samples In order to identify specific differences in the expression of genes that are associated with AD, GeneChip microarray (Affymetrix) analyses were performed with a diversity of cRNA probes derived from human brain tissue specimens from clinically and neuropathologically well characterized individuals. This technique is widely used to generate expression profiles of multiple genes and to compare populations of mRNA present in different tissue samples. In the present invention, mRNA populations present in selected post-mortem brain tissue specimens (frontal and inferior temporal cortex) were analyzed. Tissue samples were derived from individuals that could be grouped into different Braak stages reflecting the full range between healthy control individuals (Braak 0) and individuals that suffered from AD signs and symptoms (Braak 4). Verification of the differential expression of individual genes was performed applying real-time quantitative PCR using gene-specific oligonucleotides. Furthermore specific differences between healthy and disease stages were analysed at the protein level using gene product specific antibodies for immunohistochemical analyses. The methods were designed to specifically detect differences of expression levels at early Braak stages, which is indicative for pathological events occurring early in the course of the disease. Thus, said genes identified to be differential are effectively implicated in the pathogenesis of AD.

(i) Brain Tissue Dissection from Patients with AD:

Brain tissues from AD patients and age-matched control subjects, were collected. Within 6 hours post-mortem time the samples were immediately frozen on dry ice. Sample sections from each tissue were fixed in paraformaldehyde and neuropathologically staged at various stages of neurofibrillary pathology according to Braak and Braak into Braak stages (0-4). Brain areas for differential expression analysis were identified and stored at −80° C. until RNA extractions were performed.

(ii) Isolation of Total mRNA:

Total RNA was extracted from frozen post-mortem brain tissue by using the RNeasy kit (Qiagen) according to the manufacturer's protocol. The accurate RNA concentration and the RNA quality were determined applying the Eukaryote total RNA Nano LabChip system by using the 2100 Bioanalyzer (Agilent Technologies). For additional quality testing of the prepared RNA, i.e. exclusion of partial degradation and testing for DNA contamination, specifically designed intronic GAPDH oligonucleotides and genomic DNA as reference control were utilised to generate a melting curve with the LightCycler technology (Roche) as described in the supplied protocol by the manufacturer.

(iii) Probe Synthesis:

Here, total RNA was used as starting material, which had been extracted as described above (ii). For production of cDNAs, the cDNA Synthesis System was performed according to the manufacturer's protocol (Roche). cDNA samples were transcribed to cRNA and labeled with biotin applying the in vitro-transcription T7-Megascript-Kit (Ambion) according to the manufacturer's protocol. The cRNA quality was determined applying the mRNA Smear Nano LabChip system using the 2100 Bioanalyzer (Agilent Technologies). The accurate cRNA concentration was determined by photometric analysis ($OD_{260/280\,nm}$).

(iv) GeneChip Hybridization:

The purified and fragmented biotin labeled cRNA probes together with commercial spike controls (Affymetrix) bioB (1.5 pM), bioC (5 pM), bioD (25 pM), and cre (100 pM) were resuspended each at a concentration of 60 ng/µl in hybridization buffer (0.1 mg/ml Herring Sperm DNA, 0.5 mg/ml Acetylated BSA, 1×MES) and subsequently denaturated for 5 min at 99° C. Subsequently, probes were applied each onto one prehybridized (1×MES) Human Genome U133 Plus 2.0 Array (Affymetrix). Array hybridization was performed over night at 45° C. and 60 rpm. Washing and staining of the microarrays followed according to the instruction EukGe_WS2v4 (Affymetrix) controlled by GeneChip Operating System (GCOS) 1.2 (Affymetrix).

(v) GeneChip Data Analysis:

Fluorescence raw data were taken using the GeneScanner 3000 (Affymetrix) controlled by GCOS 1.2 software (Affymetrix). Data analysis was performed using DecisionSite 8.0 for Functional Genomics (Spotfire): raw data were delimitated to those that were flagged as "present" by the GCOS 1.2 software (Affymetrix); normalization of raw data was performed by percentile value; detection of differential mRNA expression profiles was performed using profile search tool of the Spotfire software. The result of such GeneChip data analysis for the gene coding for PRKX protein is shown in FIG. 1.

(vi) Verification of Differential Gene Expression by Quantitative RT-PCR:

Positive corroboration of differential PRKX gene expression was performed using the LightCycler technology (Roche). This technique features rapid thermal cycling for the polymerase chain reaction as well as real-time measurement of fluorescent signals during amplification and therefore allows for highly accurate quantification of RT-PCR products by using a kinetic, rather than endpoint readout. The relative quantity of PRKX cDNAs from the frontal and inferior temporal cortices of AD patients and age-matched control individuals respectively, were determined in a number of four up to nine tissues per Braak stage.

First, a standard curve was generated to determine the efficiency of the PCR with specific primers for the gene coding for PRKX:

Primer A, SEQ ID NO: 7, 5'-TGGGGAGGTCTACCT-TCAGTATC-3' (nucleotides 1865-1887 of SEQ ID NO: 3) and Primer B. SEQ ID NO: 8, 3'-GGGAAGATATGGGAGC-GAATT-5' (nucleotides 1939-1959 of SEQ ID NO: 3).

PCR amplification (95° C. and 1 sec, 56° C. and 5 sec, and 72° C. and 5 sec) was performed in a volume of 20 µl containing LightCycler-FastStart DNA Master SYBR Green I mix (contains FastStart Taq DNA polymerase, reaction buffer, dNTP mix with dUTP instead of dTTP, SYBR Green I dye, and 1 mM $MgCl_2$; Roche), 0.5 µM primers, 2 µl of a cDNA dilution series (final concentration of 40, 20, 10, 5, 1 and 0.5 ng human total brain cDNA; Clontech) and additional 3 mM $MgCl_2$. Melting curve analysis revealed a single peak at approximately 79.5° C. with no visible primer dimers. Quality and size of the qPCR product were determined applying the DNA 500 LabChip system using the 2100 Bioanalyzer (Agilent Technologies). A single peak at the expected size of 95 bp for the gene coding for PRKX protein was observed in the electropherogram of the sample.

In an analogous manner, the qPCR protocol was applied to determine the PCR efficiency of cyclophilin B, using the specific primers SEQ ID NO:9, 5'-ACTGAAGCAC-TACGGGCCTG-3' and SEQ ID NO:10, 5'-AGCCGTTGGT-GTCTT-TGCC-3' except for $MgCl_2$ (an additional 1 mM was added instead of 3 mM). Melting curve analysis revealed a single peak at approximately 87° C. with no visible primer dimers. Bioanalyzer analysis of the PCR product showed one single peak of the expected size (62 bp).

For calculation of the standard values, first the logarithm of the used cDNA concentration was plotted against the threshold cycle value $C_t$ for PRKX and Cyclophilin B respectively. The slopes and the intercepts of the standard curves (i.e. linear regressions) were calculated. In a second step, mRNA expression from frontal and inferior temporal cortices of controls and AD patients were analyzed in parallel. The $C_t$ values were measured and converted to ng total brain cDNA using the corresponding standard curves:

$$10^{(C_t\,value-intercept)/slope}\,[\text{ng total brain cDNA}]$$

Calculated cDNA concentration values were normalized to Cyclophilin B that was analyzed in parallel for each tested tissue probe, thus resulting values are defined as arbitrary relative expression levels. The results of such quantitative RT-PCR analysis for the gene coding for PRKX protein are shown in FIG. 2.

(vii) Statistical Analysis of Differences in mRNA Expression Comparing Tissue Samples Grouped into Different Braak Stages.

For this analysis it was proven that absolute values of real-time quantitative PCR (Lightcycler method) between different experiments at different time points are consistent enough to be used for quantitative comparisons without usage of calibrators. Cyclophilin was used as a standard for normalization in any of the qPCR experiments for more than 100 tissues. Between others it was found to be the most consistently expressed housekeeping gene in the normalization experiments. Therefore a proof of concept was done by using values that were generated for cyclophilin.

First analysis used cyclophilin values from qPCR experiments of frontal cortex and inferior temporal cortex tissues from three different donors. From each tissue the same cDNA preparation was used in all analyzed experiments. Within this analysis no normal distribution of values was achieved due to small number of data. Therefore the method of median and its 98%-confidence level was applied (Sachs L (1988) Statistische Methoden: Planung und Auswertung. Heidelberg N.Y., p. 60). This analysis revealed a middle deviation of 8.7% from the median for comparison of absolute values and a middle deviation of 6.6% from the median for relative comparison.

Second analysis used cyclophilin values from qPCR experiments of frontal cortex and inferior temporal cortex tissues from two different donors each, but different cDNA preparations from different time points were used. This analysis revealed a middle deviation of 29.2% from the median for comparison of absolute values and a middle deviation of 17.6% from the median for relative comparison. From this analysis it was concluded, that absolute values from qPCR experiments can be used, but the middle deviation from median should be taken into further considerations.

A detailed analysis of absolute values for PRKX was performed using the method of median and its 98%-confidence level. Because in contrast to the mean the calculation of the median is not affected by single data outliers; therefore latter is the method of choice for a small number of data that are distributed non-normal and/or assymetric (Sachs L (1988) Statistische Methoden: Planung und Auswertung. Heidelberg N.Y., p. 60). Therefore, absolute levels of PRKX were used after relative normalization with cyclophilin. The median as well as the 98%-confidence level was calculated for a group consisting of low level Braak stages (Braak 0-Braak 2) and the group consisting of high level Braak stages (Braak 3-Braak 4). The analysis was aimed to identify early onset of mRNA expression differences within the course of AD pathology. Said analysis described above is shown in FIG. 3.

(viii) Verification of Differential Expression of the PRKX Gene and Association with AD at the Protein Level Applying Immunohistochemical Analyses:

For immunofluorescence staining of PRKX in human brain, and for the comparison of AD-affected tissues with control tissues, post-mortem fresh-frozen frontal and temporal forebrain specimens from donors comprising patients with clinically diagnosed and neuropathologically confirmed AD at various stages of neurofibrillary pathology according to Braak and Braak (herein before and after briefly called "Braak stages") as well as age-matched non AD control individuals with neither clinical nor neuropathological signs of AD were cut at 14 μm thickness using a cryostat (Leica CM3050S). The tissue sections were air-dried at room temperature and fixed in acetone for 10 min, and air-dried again. After washing in PBS, the sections were pre-incubated with blocking buffer (10% normal horse serum, 0.2% Triton X-100 in PBS) for 30 min and then incubated with affinity-purified anti-PRKX rabbit polyclonal antibodies (Abgent/BioCat, Heidelberg, Germany) in a 1:20 dilution in blocking buffer, overnight at 4° C. After rinsing three times in 0.1% Triton X-100/PBS, the sections were incubated with AlexaFluor-488-conjugated goat anti-rabbit IgG antiserum (Jackson/Dianova, Hamburg, Germany), in a 1:1500 dilution in 1% BSA/PBS for 2 hours at room temperature and then again washed with PBS. Simultaneous staining of either (i) neuronal somata or (ii) astrocytes or (iii) microglia was performed as described above using additional mouse monoclonal antibodies against either (i) the neuron-specific somatic marker protein NeuN (Chemicon, Hampshire, UK; dilution 1:350) or (ii) the astrocyte-specific marker protein glial acidic fibrillary protein (GFAP, Abcam, Cambridge, UK; dilution 1:250) or (iii) the microglia-specific marker CD68 (Dako, Hamburg, Germany; dilution 1:100), respectively, in either case followed by a secondary Cy3-conjugated goat anti-mouse antibody (Jackson/Dianova; dilution 1:800). Staining of the nuclei was performed by incubation of the sections with 5 μM DAPI in PBS for 0.3 min. In order to block lipofuscin autofluoresence, the sections were treated with the lipophilic black dye Sudan Black B (1% w/v) in 70% ethanol for 5 min at room temperature and then sequentially dipped in 70% ethanol, destilled water and PBS. The sections were coverslipped with ProLong-Gold antifade mounting medium (Invitrogen/Molecular Probes, Karlsruhe, Germany). Microscopic images were obtained using epifluorescence or phase contrast illumination conditions using an upright microscope with a mercury-arc lamp (BX51, Olympus, Hamburg, Germany). The appropriate dichromic filter and mirror combinations (hereinafter called "channels") were used for the specific excitation of either fluorochrome (AlexaFluor-488, Cy3, DAPI) and for reading out the emitted fluorescence light resulting from the specific labeling by said antibodies or the nuclear DAPI stain. Microscopic images were digitally captured with a charge-coupled display camera and the appropriate image acquisition and processing software (ColorView-II and AnalySIS, Soft Imaging System, Olympus, Germany). Fluorescence micrographs obtained from the different channels were overlaid in order to generate simultaneous views of the above specified immunolabelings and nuclei (DAPI) in the RGB mode, e.g. for analyzing co-localization of signals from up to three different channels.

EXAMPLE 2

Analyses of PRKX Functions in AD Using Transgenic *Drosophila melanogaster*, Cell Culture Systems and Transgenic Mouse Models Human BACE transgenic flies and human TauP301L transgenic flies were generated according to Greeve et al. (Greeve et al., J. Neurosci. 2004, 24: 3899-3906) and as described in the present invention. A 1.4 kb EcoRI restriction fragment containing the entire open reading frame of the human microtubule-associated protein tau isoform NP_005901.2 (RefSeq peptide ID) was subcloned into the EcoRI site of pUAST downstream of the GAL4 binding sites UAS (Brand and Perrimon, Development 1993, 118: 401-15). A C to T (cC/Tgggaggcg) mutation was introduced to change proline (CCG) to leucine (CTG) at amino acid position 301 (TauP301L, cDNA was kindly provided by Jürgen Goetz, Götz et al., Science 2001; 24 Vol. 293. no. 5534, pp. 1491-1495). P-element-mediated germline transformation was performed as described by Spradling and Rubin (Rubin and Spradling, Science 1982, 218: 348-53; Spradling and Rubin, Science 1982, 218: 341-7). Three independent human TauP301L transgenic fly lines were generated and tested for expression of full length tau protein.

Human APP and Drosophila Presenilin transgenic flies, the UAS-APP695II and the UAS-DPsn-mutants (L235P), were kindly provided by R. Paro and E. Fortini (Fossgreen et al., Proc Natl Acad Sci USA 1998, 95: 13703-8; Ye and Fortini, J Cell Biol 1999, 146: 1351-64). Two Drosophila transgenic P-element lines which affect the expression of the endogenous pka-C3 gene of Drosophila (homolog of the human PRKX gene) were obtained from the Bloomington Drosophila Stock Center (#19832; y1 w67c23; P{EPgy2}Pka-C3EY03065 and #15581; y1 w67c23; P{EPgy2}Pka-C3EY02687). The gmr-GAL4 driver line obtained from F. Pignoni was used to achieve eye-specific expression of the transgenes.

(i) Genetics of Transgenic Flies:

Genetic crosses were set up on standard Drosophila culture medium at 25° C. Genotypes used were: w; UAS-hAPP695, UAS-hBACE437/CyO; gmr-GAL4/Tm3—w; UAS-hAPP695, UAS-hBACE437/CyO; gmr-GAL4, UAS-DPsnL235P/Tm3—w; gmr-GAL4, UAS-TauP310L—y1 w67c23; P{EPgy2}Pka-C3EY02687 and .y1 w67c23; P{EPgy2}Pka-C3EY03065 (obtained from the Bloomington Drosophila Stock Center at Indiana University).

(ii) Immunohistochemistry of Transgenic Flies:

For immunohistochemical and histological analysis, adult flies were fixed in 4% paraformaldehyde for 3 hours, washed in 1×PBS and transferred to 25% sucrose for an overnight incubation at 4° C. Flies were decapitated with a razor blade, and heads were imbedded in Tissue Tek (Sakura) and snap frozen in liquid nitrogen. 10 μm horizontal frozen sections were prepared on a cryostat (Leica CM3050S). Immunostaining was done by using the Vectastain Elite kit (Vector Laboratories) according to the instructions of the manufacturer. The following primary antibody was used to stain photoreceptor cells of the adult retina: 24B10 (alpha-chaoptin, 1:5) provided by the Developmental Studies Hybridoma Bank.

For thioflavin S staining, 10 μm paraffin embedded sections were counterstained for 5 minutes in Mayers Hemalum (Sigma), rinsed for 10 minutes in tap water and stained for 3 minutes in 1% thioflavin S (Sigma) watery solution. Slides were rinsed in several changes of distilled water, incubated for 15& minutes in 1% acetic acid, rinsed in tap water and mounted in Vectashield mounting medium (Vector laboratories). Slides were analyzed under an Olympus BX51 fluorescence microscope (430 nm excitation, 550 nm emission). Plaques were counted manually and the statistical analysis was done by using GraphPad Prism 3.02.

(iii) Abeta Measure in PKA-C3 Transgenic Flies

For immunoprecipitation of Abeta, fly heads were homogenized in 1×PBS, 5 mM EDTA, 0.5% Triton X-100 and 1× protease-inhibitor mix Complete (Roche Applied Science). Lysates were treated with antibodies as described in the antibody protocol guide from Clontech. The antibody mab 6E10 (anti-Abeta1-16, Signet Pathology Systems) was used for immunoprecipitation. Samples were separated on 10-20% gradient Novex Tris-Tricine gels (Invitrogen) and blotted onto Protran BA 79 Cellulose nitrate membranes (0.1 μm, Schleicher/Schuell, Dassel, Germany). Detection of beta-amyloid was performed as described (Ida et al., J Biol Chem 1996, 271: 22908-14) using mab 6E10 and goat anti-mouse peroxidase conjugated secondary antibody (Dianova).

(iv) Expression Analysis of PKA-C3 Transgenic Flies

For the detection of Drosophila pka-C3 expression in transgenic Drosophila a reverse transcriptase PCR (RT-PCR Reaction) reaction was performed using pka-C3 specific primers (5'-AGAGGCATCGCTGGTTCAAG, 3'-GTA-CATCGGGCAAAATTGGTG) as described in the present invention (Example 1 (vi)).

(v) pS214 Specific ELISA

Ten fly heads were homogenized in 50 μl cell lysis buffer containing phosphatase inhibitors (10 mM Tris, pH7.4; 100 mM NaCl; 1 mM EDTA; 1 mM EGTA; 1 mM NaF; 20 mM Na4P2O7; 2 mM Na3VO4; 1% Triton X-100; 10% glycerol; 0.1% SDS; 0.5% deoxycholate, 10 μM okadaic acid). Lysates were centrifuged 3 min at 13000 rpm and the supernatant was used at a 1:100 dilution to determine phosphorylation at S214 of TauP301L by using a Human Tau [pS214] Immunoassay Kit (Biosource) according to the manufacturer's protocol. The amount of phosphorylated S214 was normalized to the total amount of TauP301L by using a Human Tau [total] Immunoassay Kit (Biosource). The same lysates were used at a dilution of 1:8000. GraphPad Prism 3.02 was used for the statistical analysis.

(vi) Generation of Cell Lines Inducibly Expressing PRKX:

The tet-repressor encoded on the pcDNA6/TR-vector (purchased from Invitrogen #K1020-01) was transfected into the H4-neuroglioma cell line expressing the Swedish mutant amyloid precursor protein (APP) and clonal cell lines were isolated after the addition of the antibiotic blasticidin. The resulting cell line was then used to introduce PRKX under the control of the tet-operator sequence into the cells. Expression of PRKX can be induced by the addition of 1 μg/ml tetracycline following the manufacturer's instructions (Invitrogen #K1020-01).

(vii) Generation of Transgenic Mice Expressing PRKX:

PRKX transgenic mice were generated to specifically expressing human PRKX cDNA in neuronal cells. For this purpose the open reading frame of the human PRKX (ORF PRKX) cDNA was cloned into the murine Thy1.2 expression cassette containing a brain-specific Thy1 regulatory sequence (Thy1.2 promoter+regulatory elements) to direct neuronal specific expression and thus, causes expression only in brain cells (Luthi and van der Putten, J. Neuroscience 1997, 17:4688-4699). The transgene was cloned into a Rosa26 targeting vector in order to integrate the sequences into the Rosa26 gene locus (mouse Rosa beta geo 26 gene on chromosome 6; J:39814, Seibler et al, Nucleic Acids Research 2003, 31: e12). 5'prime of the transgene a Neo selection marker was placed (see FIG. 20). The Neo cassette contains a splice acceptor allowing expression of the Neo selection marker driven by the Rosa promoter from the endogenous Rosa26 gene (Friedrich and Soriano, Genes Dev. 1991, 5:1513-1523; Zambrowicz et al., Proc Natl Acad Sci USA, 94:3789-3794). 3'prime of the Neo marker a poly A signal (pA) will stop transcription and the influence of the Rosa promoter. The targeting vector contains Rosa26 homology sequences from genomic 129S6 DNA to allow homologous recombination into the Rosa26 gene locus. The short homology arm (SA) consists of approximately 1.1 kb, the long homology arm (LA) consists of about 4.3 kb.

The targeting vector was cloned and further, transfected into C57Bl/6N mouse embryonal stem (ES) cells (Hogan et al., Manipulating the Mouse Embryo: A Laboratory Manual, Cold Spring Harbor Laboratory Press, Cold Spring Harbor, N.Y., 1994 and Jackson and Abbott, Mouse Genetics and Transgenics: A Practical Approach, Oxford University Press, Oxford, England, 1999). After homologous recombination, targeted ES cell clones were identified by Southern Blot analysis and injected into blastocyst to generate chimeric mice using standard techniques (Tymms and Kola, Gene Knock Out Protocols, Humana Press 2001). After successful transmission of the germlne of the chimeric mice generated, the animals were crossed to a transgenic AD mouse model to produce transgenic PRKX mice on an AD background.

The invention claimed is:

1. A method of diagnosing Alzheimer's disease at Braak stage 4 or above in a test subject, comprising the steps of:
   (a) determining a level of a transcription product of a gene coding for PRKX protein having SEQ ID NO: 1 in both a brain tissue sample of an inferior temporal cortex obtained from said test subject and a brain tissue sample of an inferior temporal cortex obtained from a healthy subject,
   (b) comparing said level between the inferior temporal cortex from the test subject and the inferior temporal cortex from the healthy subject, and
   (c) diagnosing Alzheimer's disease at Braak stage 4 or above by determining whether the said level of the test subject is higher than that of the healthy subject.

* * * * *

UNITED STATES PATENT AND TRADEMARK OFFICE
CERTIFICATE OF CORRECTION

PATENT NO. : 8,114,620 B2  
APPLICATION NO. : 11/921225  
DATED : February 14, 2012  
INVENTOR(S) : Johannes Pohlner et al.

Page 1 of 1

It is certified that error appears in the above-identified patent and that said Letters Patent is hereby corrected as shown below:

On the Title Page:

Please insert the following:

-- Related U.S. Application Data

(60) Provisional application No. 60/685,525, filed on May 31, 2005. --

On the first page of the Specification:

Please insert the following:

-- This application claims the benefit of U.S. Patent Application No. 60/685,525, filed May 31, 2005. --

Signed and Sealed this
Thirty-first Day of July, 2012

David J. Kappos
*Director of the United States Patent and Trademark Office*